United States Patent
Wik et al.

(10) Patent No.: US 8,076,115 B2
(45) Date of Patent: Dec. 13, 2011

(54) POLYPEPTIDES HAVING PHYTASE ACTIVITY AND POLYNUCLEOTIDES ENCODING SAME

(75) Inventors: Monica Takamiya Wik, Horsholm (DK); Carsten Sjoholm, Allerod (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/842,426

(22) Filed: Jul. 23, 2010

(65) Prior Publication Data

US 2010/0287634 A1 Nov. 11, 2010

Related U.S. Application Data

(62) Division of application No. 11/574,715, filed as application No. PCT/DK2005/000631 on Oct. 4, 2005, now Pat. No. 7,833,768.

(60) Provisional application No. 60/616,569, filed on Oct. 6, 2004, provisional application No. 60/616,586, filed on Oct. 6, 2004, provisional application No. 60/638,553, filed on Dec. 23, 2004, provisional application No. 60/638,714, filed on Dec. 23, 2004.

(30) Foreign Application Priority Data

| Oct. 4, 2004 | (DK) | 2004 01514 |
| Oct. 4, 2004 | (DK) | 2004 01515 |
| Dec. 23, 2004 | (DK) | 2004 01998 |
| Dec. 23, 2004 | (DK) | 2004 01999 |

(51) Int. Cl.
*C07K 14/00* (2006.01)
*C12N 9/16* (2006.01)
*C12Q 1/44* (2006.01)
*A23J 1/00* (2006.01)
*C12N 15/00* (2006.01)
*C12P 21/00* (2006.01)

(52) U.S. Cl. ...... 435/196; 435/19; 435/69.1; 435/320.1; 530/350; 426/63; 426/656

(58) Field of Classification Search ............ 435/196, 435/19, 69.1, 320.1; 530/350; 426/63
See application file for complete search history.

(56) References Cited

U.S. PATENT DOCUMENTS 5,612,055 A 3/1997 Bedford et al.

FOREIGN PATENT DOCUMENTS

| KR | 2004/045267 | 6/2004 |
| WO | WO 00/64247 A1 | 11/2000 |
| WO | WO 00/71728 A1 | 11/2000 |
| WO | WO 03/057248 A1 | 7/2003 |
| WO | WO 2004/085638 A1 | 10/2004 |
| WO | WO 2006/037328 A1 | 4/2006 |
| WO | WO 2006/038062 A1 | 4/2006 |
| WO | WO 2006/038128 A2 | 4/2006 |
| WO | WO 2006/063588 A1 | 6/2006 |

OTHER PUBLICATIONS

Zinin et al., GenBank accession No. AAR89622, Sep. 1, 2004.*
Ausubel, Current Protocols in Molecular Biology, Hybridization Analysis of DNA Blots, pp. 2.10.1-2.10.16 (1993).
Branden et al., Introduction to Protein Structure, Garden Publishing In., New York, p. 247 (1991).
Guo et al., PNAS, vol. 101, No. 25, pp. 9205-9210 (2004).
Huang et al., Database UniProt, Accession No. Q003Y3 (2006).
Kim et al., Biotechnology Letters, vol. 25, pp. 1231-1234 (2003).
Kim et al., Database Geneseq, Accession No. ADU50736 (2004).
Kim et al., Database Geneseq, Accession No. ADU50737 (2004).
Kim et al., Database WPIDS, Accession No. 2004-673753 (2004).
Seffernick et al., Journal of Bacteriology, vol. 183, No. 8, pp. 2405-2410 (2001).
Witkowski et al., Biochemistry, vol. 38, pp. 11643-11650 (1999).
Zinin et al., Biotekhnologiya, vol. 2, pp. 3-10 (2003).
Zinin et al., Database EMBL, Accession No. AY390262 (2004).

\* cited by examiner

*Primary Examiner* — Delia Ramirez
(74) *Attorney, Agent, or Firm* — Elias Lambiris

(57) ABSTRACT

The invention relates to *Citrobacter* phytases derived from *Citrobacter amalonaticus*, *Citrobacter gillenii*, and related phytases. The phytases belong to the acid histidine phosphatase family, are acid-stable, and expectedly of a high specific activity. The invention also relates to the corresponding DNA, the recombinant and wild-type production of the phytases, as well as the use thereof, in particular in animal feed.

17 Claims, No Drawings

US 8,076,115 B2

POLYPEPTIDES HAVING PHYTASE ACTIVITY AND POLYNUCLEOTIDES ENCODING SAME

CROSS-REFERENCE TO RELATED APPLICATIONS

This application is a divisional of U.S. application Ser. No. 11/574,715 filed on Mar. 5, 2007, now U.S. Pat. No. 7,833,768, which is a 35 U.S.C. 371 national application of PCT/DK2005/000631 filed Oct. 4, 2005, which claims priority or the benefit under 35 U.S.C. 119 of Danish application nos. PA 2004 01514, PA 2004 01515, PA 2004 01998, and PA 2004 01999 filed Oct. 4, 2004, Oct. 4, 2004, Dec. 23, 2004 and Dec. 23, 2004, respectively, and U.S. provisional application Nos. 60/616,569, 60/616,586, 60/638,553, and 60/638,714 filed Oct. 6, 2004, Oct. 6, 2004, Dec. 23, 2004, and Dec. 23, 2004, respectively, the contents of which are fully incorporated herein by reference.

BACKGROUND OF THE INVENTION

1. Field of the Invention

The present invention relates to isolated polypeptides having phytase activity and isolated polynucleotides encoding the polypeptides. The polypeptides are related to *Citrobacter* phytases derived from *Citrobacter amalonaticus* and *Citrobacter gillenii*, the amino acid sequence of which are shown in the appended sequence listing as SEQ ID NOs: 4 and 6. The invention also relates to nucleic acid constructs, vectors, and host cells comprising the polynucleotides as well as methods for producing and using the polypeptides, in particular within animal feed.

2. Description of the Related Art

Phytases are well-known enzymes, as are the advantages of adding them to foodstuffs for animals, including humans. Phytases have been isolated from very many sources, including a number of fungal and bacterial strains.

The acid histidine phosphatase appA of *Escherichia coli* as well as other gram-negative bacterial phytases are known to have a high specific activity.

The production by *Citrobacter braakii* YH-15 of an intracellular phytase is reported by Kim et al., 2003, *Biotechnology Letters* 25: 1231-1234. KR-2004-A-045267 and WO 2004/085638 disclose, as SEQ ID NO: 7, the amino acid sequence of a phytase from *Citrobacter braakii* YH-15, deposited as KCCM 10427. WO 2004/085638 was published on Jul. 10, 2004, viz. after the first priority date of the present application.

It is an object of the present invention to provide alternative polypeptides having phytase activity and polynucleotides encoding the polypeptides. The polypeptides of the invention are preferably of amended, more preferably improved, properties, for example of a different substrate specificity, of a higher specific activity, of an increased stability (such as acid-stability, heat-stability, and/or protease stability, in particular pepsin stability), of an amended pH optimum (such as a lower, or higher pH optimum), and/or of an improved performance in animal feed (such as an improved release and/or degradation of phytate).

SUMMARY OF THE INVENTION

The present invention relates to polypeptides having phytase activity, selected from the group consisting of: (a) a polypeptide having an amino acid sequence which has at least 75% identity with (i) amino acids 1 to 409 of SEQ ID NO: 2, (ii) the mature polypeptide part of SEQ ID NO: 2, (iii) amino acids 1 to 410 of SEQ ID NO: 4, (iv) the mature polypeptide part of SEQ ID NO: 4, (v) amino acids 1 to 414 of SEQ ID NO: 6, and/or (vi) the mature polypeptide part of SEQ ID NO: 6; (b) a polypeptide which is encoded by a polynucleotide which hybridizes under at least medium stringency conditions with (i) nucleotides 67 to 1293 of SEQ ID NO: 1, (ii) the mature polypeptide encoding part of SEQ ID NO: 1, (iii) nucleotides 67 to 1296 of SEQ ID NO: 3, (iv) the mature polypeptide encoding part of SEQ ID NO: 3, (v) nucleotides 67 to 1308 of SEQ ID NO: 5, (vi) the mature polypeptide encoding part of SEQ ID NO: 5, and/or (vii) a complementary strand of any one of (i), (ii), (iii), (iv), (v), or (vi); (c) a variant of any one of the polypeptides of (a)(i)-(a)(vi), comprising a conservative substitution, deletion, and/or insertion of one or more amino acids; and (d) a fragment of any one of the polypeptides of (a)(i)-(a)(vi).

The invention also relates to isolated polynucleotides encoding a polypeptide having phytase activity, selected from the group consisting of: (a) a polynucleotide encoding a polypeptide having an amino acid sequence which has at least 75% identity with any one of (i) amino acids 1 to 409 of SEQ ID NO: 2, (ii) amino acids 1 to 410 of SEQ ID NO: 4, and/or (iii) amino acids 1 to 414 of SEQ ID NO: 6; (b) a polynucleotide having at least 75% identity with any one of (i) nucleotides 67 to 1293 of SEQ ID NO: 1, (ii) nucleotides 67 to 1296 of SEQ ID NO: 3, and/or (iii) amino acids 67 to 1308 of SEQ ID NO: 5; and (c) a polynucleotide which hybridizes under at least medium stringency conditions with (i) nucleotides 67 to 1293 of SEQ ID NO: 1, (ii) the mature polypeptide encoding part of SEQ ID NO: 1, (iii) nucleotides 67 to 1296 of SEQ ID NO: 3, (iv) the mature polypeptide encoding part of SEQ ID NO: 3, (v) nucleotides 67 to 1308 of SEQ ID NO: 5, (vi) the mature polypeptide encoding part of SEQ ID NO: 5, and/or (vii) a complementary strand of any one of (i), (ii), (iii), (iv), (v), or (vi).

The invention also relates to nucleic acid constructs, recombinant expression vectors, and recombinant host cells comprising the polynucleotides.

The invention also relates to methods for producing such polypeptides having phytase activity comprising (a) cultivating a recombinant host cell comprising a nucleic acid construct comprising a polynucleotide encoding the polypeptide under conditions conducive for production of the polypeptide; and (b) recovering the polypeptide.

The invention also relates to methods of using the polypeptides of the invention in animal feed, as well as animal feed and animal feed additive compositions containing the polypeptides.

The invention further relates to a nucleic acid construct comprising a gene encoding a protein operably linked to a nucleotide sequence encoding a signal peptide consisting of (i) nucleotides 1 to 66 of SEQ ID NO: 1, (ii) nucleotides 1 to 66 of SEQ ID NO: 3, or (iii) nucleotides 1 to 66 of SEQ ID NO: 5; wherein the gene is foreign to the nucleotide sequence.

Definitions

Phytase activity: In the present context a polypeptide having phytase activity (a phytase) is an enzyme which catalyzes the hydrolysis of phytate (myo-inositol hexakis-phosphate) to (1) myo-inositol and/or (2) mono-, di-, tri-, tetra- and/or penta-phosphates thereof and (3) inorganic phosphate.

The ENZYME site at the internet is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch, The ENZYME database, 2000, *Nucleic Acids Res.* 28: 304-305). See also the handbook Enzyme Nomenclature from NC-IUBMB, 1992).

According to the ENZYME site, three different types of phytases are known: A 3-phytase (myo-inositol hexaphosphate 3-phosphohydrolase, EC 3.1.3.8), a 6-phytase (myo-inositol hexaphosphate 6-phosphohydrolase, EC 3.1.3.26), and a 5-phytase (EC 3.1.3.72). For the purposes of the present invention, all types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R-H-G-X-R-X-P, wherein X designates any amino acid (see amino acids 16 to 22 of SEQ ID NO: 2, amino acids 16 to 22 of SEQ ID NO: 4, and amino acids 16 to 22 of SEQ ID NO: 6).

For the purposes of the present invention the phytase activity is determined in the unit of FYT, one FYT being the amount of enzyme that liberates 1 micro-mol inorganic orthophosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are the FYT and FTU assays described in Example 1 of WO 00/20569. FTU is for determining phytase activity in feed and premix. Phytase activity may also be determined using the phytase assay of Example 4 herein.

The pH-optimum of a polypeptide of the invention is determined by incubating the phytase at various pH-values, using a substrate in a pre-determined concentration and a fixed incubation temperature. The pH-optimum is then determined from a graphical representation of phytase activity versus pH. In a particular embodiment, the FYT assay is used, viz. the substrate is 5 mM sodium phytate, the reaction temperature 37° C., and the activity is determined in FYT units at various pH-values, for example pH 2-12, using suitable buffers, such as: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0, 11.0, and 12.0 with HCl or NaOH. In another particular embodiment, the phytase assay of Example 4 is used, viz. the substrate is 0.5 mM, preferably 5 mM, Na-phytate, which is dissolved in a buffer of the desired pH (such as those mentioned above), and soluble phosphate is determined by complexation with molybdate/iron and measurement of optical density at 750 nm. Blind: 20 ul sample, 100 ul substrate and 120 ul color reagent is mixed, incubated 5 min at 37° C. and $OD_{Blind}$ measured at 750 nm. Sample: 20 ul sample, 100 ul substrate is mixed, incubated 30 min at 37° C., 120 ul color reagent is added, incubated 5 min at 37° C., and $OD_{sample}$ is measured at 750 nm. The phytase activity is measured as $OD=OD_{sample}-OD_{Blind}$. A relatively low pH-optimum means a pH-optimum below pH 5.0, for example below pH 4.5, 4.0, 3.5, 3.0, 2.5, or even below 2.0. A relatively high pH-optimum means a pH-optimum above pH 5.0, for example above pH 5.5, 6.0, 6.5, 7.0, 7.5, 8.0, 8.5, or even above 9.0.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences, as well as the degree of identity between two nucleotide sequences, is determined by the program "align" which is a Needleman-Wunsch alignment (i.e., global alignment), useful for both protein and DNA alignments. The default scoring matrix BLOSUM50 and the default identity matrix are used for protein and DNA alignments respectively. The penalty for the first residue in a gap is −12 for proteins and −16 for DNA. While the penalties for additional residues in a gap are −2 for proteins and −4 for DNA.

"Align" is part of the FASTA package version v20u6 (see Pearson and Lipman, 1988, "Improved Tools for Biological Sequence Analysis", *PNAS* 85:2444-2448, and Pearson, 1990, "Rapid and Sensitive Sequence Comparison with FASTP and FASTA," *Methods in Enzymology* 183: 63-98). FASTA protein alignments use the Smith-Waterman algorithm with no limitation on gap size (see "Smith-Waterman algorithm", Smith and Waterman, 1981, *J. Mol. Biol.* 147: 195-197).

The Needleman-Wunsch algorithm is described in Needleman and Wunsch, 1970, *Journal of Molecular Biology* 48: 443-453, and the align program by Myers and W. Miller, 1988, "Optimal Alignments in Linear Space" *CABIOS* (computer applications in the biosciences) 4: 11-17.

The degree of identity between the target (or sample, or test) sequence and a specified sequence (e.g., amino acids 1 to 409 of SEQ ID NO: 2) may also be determined as follows: The sequences are aligned using the program "align." The number of perfect matches ("N-perfect-match") in the alignment is determined (a perfect match means same amino acid residue in same position of the alignment, usually designated with a "|" in the alignment). The length of the specified sequence (the number of amino acid residues) is determined ("N-specified", in the example mentioned above=411). The degree of identity is calculated as the ratio between "N-perfect-match" and "N-specified" (for conversion to percentage identity, multiply by 100).

In an alternative embodiment, the degree of identity between a target (or sample, or test) sequence and the specified sequence (e.g., amino acids 1 to 409 of SEQ ID NO: 2) is determined as follows: The two sequences are aligned using the program "align." The number of perfect matches ("N-perfect-match") in the alignment is determined (a perfect match means same amino acid residue in same position of the alignment, usually designated with a "|" in the alignment). The common length of the two aligned sequences is also determined, viz. the total number of amino acids in the overlapping part of the alignment ("N-overlap"). The degree of identity is calculated as the ratio between "N-perfect-match" and "N-overlap" (for conversion to percentage identity, multiply by 100). In one embodiment, N-overlap includes trailing and leading gaps created by the alignment, if any. In another embodiment, N-overlap excludes trailing and leading gaps created by the alignment, if any.

In another alternative embodiment, the degree of identity between a target (or sample, or test) sequence and a specified sequence (e.g., amino acids 1 to 409 of SEQ ID NO: 2) is determined as follows: The sequences are aligned using the program "align." The number of perfect matches ("N-perfect-match") in the alignment is determined (a perfect match means same amino acid residue in same position of the alignment, usually designated with a "|" in the alignment). The length of the target sequence (the number of amino acid residues) is determined ("N-target"). The degree of identity is calculated as the ratio between "N-perfect-match" and "N-target" (for conversion to percentage identity, multiply by 100).

Preferably, the overlap is at least 20% of the specified sequence ("N-overlap" as defined above, divided by the number of the amino acids in the specified sequence ("N-specified"), and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the specified sequence end up being included in the overlap, when the sample sequence is aligned to the specified sequence.

In the alternative, the overlap is at least 20% of the target (or sample, or test) sequence ("N-overlap" as defined above, divided by "N-target" as defined above, and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the target sequence end up being included in the overlap, when aligned against the specified sequence.

Polypeptide Fragment: The term "polypeptide fragment" is defined herein as a polypeptide having one or more amino acids deleted from the amino and/or carboxyl terminus of the mature peptide part of SEQ ID NO: 2, SEQ ID NO: 4, SEQ ID NO: 6, or a homologous sequence of any of these, wherein the fragment has phytase activity. In particular embodiments, the fragment contains at least 350, 360, 370, 380, 390, 400, 405, or at least 410 amino acid residues.

Subsequence: The term "subsequence" is defined herein as a nucleotide sequence having one or more nucleotides deleted from the 5' and/or 3' end of the mature peptide encoding part of SEQ ID NO: 1, SEQ ID NO: 3, SEQ ID NO: 5, or a homologous sequence of any of these, wherein the subsequence encodes a polypeptide fragment having phytase activity. In particular embodiments, the subsequence contains at least 1050, 1080, 1110, 1140, 1170, 1200, 1215, or at least 1230 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Mature polypeptide part: When used herein the terms "mature polypeptide part" or "mature peptide part" refer to that part of the polypeptide which is secreted by a cell which contains, as part of its genetic equipment, a polynucleotide encoding the polypeptide. In other words, the mature polypeptide part refers to that part of the polypeptide which remains after the signal peptide part is cleaved off once it has fulfilled its function of directing the encoded polypeptide into the cell's secretory pathway. The predicted signal peptide part of SEQ ID NO: 2, SEQ ID NO: 4, and SEQ ID NO: 6 is amino acids −22 to −1 thereof, which means that the predicted mature polypeptide part of SEQ ID NO: 2, 4, and 6, respectively, corresponds to amino acids 1 to 409, 1 to 410, and 1 to 414 thereof, respectively. However, a slight variation may occur from host cell to host cell, and therefore the expression mature polypeptide part is preferred.

Mature polypeptide encoding part: When used herein the term "mature polypeptide encoding part" or "mature polypeptide coding sequence" refers to that part of the polynucleotide encoding the polypeptide which encodes the mature polypeptide part. For example, for SEQ ID NOs: 1, 3, and 5 the predicted mature polypeptide encoding parts correspond to nucleotides 67 to 1293, 67 to 1296, and 67 to 1308 thereof, respectively (encoding amino acids 1 to 409 of SEQ ID NO: 2, amino acids 1 to 410 of SEQ ID NO: 4, and amino acid 1 to 414 of SEQ ID NO: 6, respectively).

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptides consisting of the amino acids 1 to 409 of SEQ ID NO: 2, amino acids 1 to 410 of SEQ ID NO: 4, or amino acid 1 to 414 of SEQ ID NO: 6, as well as genetic manipulation of the DNA encoding these polypeptides. The modification(s) can be substitution(s), deletion(s) and/or insertions(s) of the amino acid(s) as well as replacement(s) of amino acid side chain(s).

Artificial variant: When used herein, the term "artificial variant" means a polypeptide having phytase activity produced by an organism expressing a modified nucleotide sequence of SEQ ID NO: 1, SEQ ID NO: 3, or SEQ ID NO: 5. The modified nucleotide sequence is obtained through human intervention by modification of the nucleotide sequence disclosed in SEQ ID NOs: 1, 3, and 5.

DETAILED DESCRIPTION OF THE INVENTION

Polypeptides Having Phytase Activity

In a first aspect, the present invention relates to isolated polypeptides having an amino acid sequence which has a degree of identity to amino acids 1 to 409 of SEQ ID NO: 2, amino acids 1 to 410 of SEQ ID NO: 4, or amino acids 1 to 414 of SEQ ID NO: 6 (i.e., the mature polypeptides) of at least 75%, and which have phytase activity (hereinafter "homologous polypeptides"). In particular embodiments, the degree of identity is at least 76, 77, 78, 79, 80, 81, 82, 83, 84, 85, 86, 87, 88, 89, 90, 91, 92, 93, 94, 95, 96, 97, 98, or at least 99%.

In other particular embodiments, the homologous polypeptides have an amino acid sequence which differs by twenty, eighteen, sixteen, fourteen, twelve, ten, eight, six, five, four, three, two, or by one amino acid from either of amino acids 1 to 409 of SEQ ID NO: 2, amino acids 1 to 410 of SEQ ID NO: 4, or amino acids 1 to 414 of SEQ ID NO: 6.

In alternative embodiments, the degree of identity to amino acids 1 to 409 of SEQ ID NO: 2, amino acids 1 to 410 of SEQ ID NO: 4, or amino acids 1 to 414 of SEQ ID NO: 6 (i.e., the mature polypeptides) is at least 60, 62, 65, 66, 68, 70, 71, 72, 73, or at least 74%.

In particular embodiments, the polypeptide of the present invention comprises the amino acid sequence of SEQ ID NOs: 2, 4, or 6, or is an allelic variant thereof; or a fragment thereof that has phytase activity. In still further particular embodiments, the polypeptide comprises amino acids 1 to 409 of SEQ ID NO: 2, amino acids 1 to 410 of SEQ ID NO: 4, or amino acids 1 to 414 of SEQ ID NO: 6, or an allelic variant thereof; or a fragment thereof that has phytase activity.

In a second aspect, the present invention relates to isolated polypeptides having phytase activity which are encoded by polynucleotides which hybridize under at least medium, preferably medium, stringency conditions with (i) nucleotides 67 to 1293 of SEQ ID NO: 1, nucleotides 67 to 1296 of SEQ ID NO: 3, or nucleotides 67 to 1308 of SEQ ID NO: 5; (ii) the mature polypeptide encoding parts of SEQ ID NOs: 1, 3, or 5; and/or (iii) a complementary strand of any one of (i), and (ii), and/or (iv) a subsequence of (i), (ii), or (iii) (J. Sambrook, E. F. Fritsch, and T. Maniatus, 1989, Molecular Cloning, A Laboratory Manual, 2d edition, Cold Spring Harbor, N.Y.). A subsequence of SEQ ID NO: 1, 3, or 5 contains at least 100 contiguous nucleotides or preferably at least 200 contiguous nucleotides. Moreover, the subsequence may encode a polypeptide fragment which has phytase activity.

In particular embodiments, the hybridization takes place under at least medium-high, at least high, or at least very high stringency conditions; preferably under medium-high, high, or very high stringency conditions.

In alternative embodiments, the hybridization is conducted under very low, or low stringency conditions.

The nucleotide sequences of SEQ ID NO: 1, 3, or 5, or a subsequence of any of these, as well as the amino acid sequences of SEQ ID NO: 2, 4, or 6 may be used to design a nucleic acid probe to identify and clone DNA encoding polypeptides having phytase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA library prepared from such other organisms may, therefore, be screened for DNA which hybridizes with the probes described above and which encodes a polypeptide having phytase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, 3, or 5, or a subsequence of any of these, the carrier material is used in a Southern blot.

For purposes of the present invention, hybridization indicates that the nucleotide sequence hybridizes to a labeled nucleic acid probe corresponding to the nucleotide sequences shown in SEQ ID NO: 1, 3, and/or 5, their complementary strands, or subsequences thereof, under very low to very high stringency conditions. Molecules to which the nucleic acid probe hybridizes under these conditions can be detected using X-ray film.

In a particular embodiment, the nucleic acid probe is any one of SEQ ID NOs: 1, 3, 5, or 7-18. In another particular embodiment, the nucleic acid probe is the complementary strand of nucleotides 67 to 450, nucleotides 450 to 900, or nucleotides 900 to 1293 of SEQ ID NO: 1, 3 or 5. In a further particular embodiment, the nucleic acid probe is a polynucleotide sequence which encodes the polypeptide of SEQ ID NO: 2, 4, or 6, or a subsequence of any of these. In a still further particular embodiment, the nucleic acid probe is SEQ ID NO: 1, SEQ ID NO: 3, or SEQ ID NO: 5, in particular the mature polypeptide coding regions thereof.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48: 1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[\text{Na}^+]) + 0.41(\% \, G+C) - 0.72(\% \, \text{formamide})$$

"G+C" designates the content of nucleotides G and T in the probe. For medium stringency, for example, the formamide is 35% and the Na$^+$ concentration for 5×SSPE is 0.75 M.

In a third aspect, the present invention relates to isolated polypeptides having phytase activity, and the following physicochemical properties (as analyzed on the substantially pure polypeptides):
(i) a high specific activity, such as a specific activity on phytate of at least 50% of the specific activity of *E. coli* appA (SPTREMBL:Q8GN88), the specific activity being preferably measured in the units of FYT per mg phytase enzyme protein;
(ii) acid-stability; such as
   (a) at least 60%, preferably at least 65%, at least 70%, or at least 75%, residual activity after incubation over night at 37° C. in glycine/hydrochloric acid buffer pH 2.2, relative to the residual activity after incubation over night at 37° C. in HEPES buffer pH 7.0;
   (b) at least 80%, preferably at least 85%, at least 90%, or at least 95%, residual activity after incubation over night at 37° C. in glycine/hydrochloric acid buffer pH 3.0, relative to the residual activity after incubation over night at 37° C. in HEPES buffer pH 7.0; and/or
   (c) a residual phytase activity after 2 hours incubation at a temperature of 25, 30, 35, or 37° C., preferably 37° C., and a pH of 2.2, 2.4, 2.5, 2.6, 2.8, 3.0, 3.2, 3.4, or 3.5, preferably glycine/hydrochloric acid buffers of pH 2.2, or 3.0, of at least 50%, compared to the residual activity of *E. coli* appA (SPTREMBL:Q8GN88);
(iii) heat-stability, such as a residual phytase activity after 0.5, 1, 1.5, or 2 hours, preferably 0.5 hours, of incubation at a pH of 5.5 and a temperature of 55, 60, 65, 70, 75, 80, 85 or 95° C., preferably 70° C., of at least 50%, compared to the residual activity of *E. coli* appA (SPTREMBL:Q8GN88);
(iv) protease-stability, such as a residual phytase activity after 0.5, 1, 1.5, or 2 hours, preferably 1 hour, incubation at a temperature of 20, 25, 30, 35, or 37° C., preferably 37° C., and a pH of 5.5, in the presence of 0.1 mg/ml pepsin, of at least 50%, compared to the residual activity of *E. coli* appA (SPTREMBL:Q8GN88); and/or
(v) a pH-optimum below pH 5.0, for example below pH 4.5, 4.0, 3.5, 3.0, 2.5, or even below 2.0, determined using the FYT assay, and/or using the assay of Example 4, as described hereinbefore.

In particular embodiments of aspect (i) above, the specific activity is at least 60, 70, 80, 90, 100, 110, 120, 130, 140, or at least 150% of the specific activity of *E. coli* appA. In particular embodiments of each of aspects (ii) to (iv) above, the residual activity is at least 60, 70, 80, 90, 100, 110, 120, 130, 140, or at least 150% of the residual activity of *E. coli* appA, or, for embodiment (ii)(a) and (ii)(b), relative to the residual activity at pH 7.0.

In a fourth aspect, the present invention relates to artificial variants comprising a conservative substitution, deletion, and/or insertion of one or more amino acids of SEQ ID NO: 2, 4, or 6, or the mature polypeptides of any of these. An insertion can be inside the molecule, and/or at the N- and/or C-terminal end of the molecule in which case it is also designated extension. Preferably, amino acid changes are of a minor nature, that is conservative amino acid substitutions; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain domain—in other words: Changes that do not significantly affect the folding and/or activity of the protein.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine).

Other examples of conservative substitutions are substitutions of the 20 standard amino acids with non-standard amino acids (such as 4-hydroxyproline, 6-N-methyl lysine, 2-aminoisobutyric acid, isovaline, and alpha-methyl serine). Conservative substitutions may also include a substitution into amino acids that are not encoded by the genetic code, and unnatural amino. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., phytase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions (preferably conservative substitutions), deletions and/or insertions in the sequence of amino acids 1 to 409 of SEQ ID NO: 2, amino acids 1 to 410 of SEQ ID NO: 4, or amino acids 1 to 414 of SEQ ID NO: 6 is at most 10, preferably at most 9, more preferably at most 8, more preferably at most 7, more preferably at most 6, more preferably at most 5, more preferably at most 4, even more preferably at most 3, most preferably at most 2, and even most preferably 1.

The total number of amino acid substitutions, deletions and/or insertions of amino acids 1 to 409 of SEQ ID NO: 2, amino acids 1 to 410 of SEQ ID NO: 4, or amino acids 1 to 414 of SEQ ID NO: 6 is 10, preferably 9, more preferably 8, more preferably 7, more preferably at most 6, more preferably at most 5, more preferably 4, even more preferably 3, most preferably 2, and even most preferably 1. In the alternative, the total number of amino acid substitutions (preferably conservative substitutions), deletions and/or insertions in the sequence of amino acids 1 to 409 of SEQ ID NO: 2, 1 to 410 of SEQ ID NO: 4, or 1 to 414 of SEQ ID NO: 6, is at most 50, 45, 40, 35, 30, 25, 20, 19, 18, 17, 16, 15, 14, 13, 12, or at most 11.

In a specific embodiment, the polypeptide of the invention is a low-allergenic variant, designed to invoke a reduced immunological response when exposed to animals, including man. The term immunological response is to be understood as any reaction by the immune system of an animal exposed to the polypeptide. One type of immunological response is an allergic response leading to increased levels of IgE in the exposed animal. Low-allergenic variants may be prepared using techniques known in the art. For example the polypeptide may be conjugated with polymer moieties shielding portions or epitopes of the polypeptide involved in an immunological response. Conjugation with polymers may involve in vitro chemical coupling of polymer to the polypeptide, e.g., as described in WO 96/17929, WO 98/30682, WO 98/35026, and/or WO 99/00489. Conjugation may in addition or alternatively thereto involve in vivo coupling of polymers to the polypeptide. Such conjugation may be achieved by genetic engineering of the nucleotide sequence encoding the polypeptide, inserting consensus sequences encoding additional glycosylation sites in the polypeptide and expressing the polypeptide in a host capable of glycosylating the polypeptide, see, e.g., WO 00/26354. Another way of providing low-allergenic variants is genetic engineering of the nucleotide sequence encoding the polypeptide so as to cause the polypeptide to self-oligomerize, effecting that polypeptide monomers may shield the epitopes of other polypeptide monomers and thereby lowering the antigenicity of the oligomers. Such products and their preparation is described, e.g., in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the polypeptide by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

Sources of Polypeptides Having Phytase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, or a *Streptomyces* polypeptide; or a gram negative bacterial polypeptide, e.g., an *Escherichia coli, Yersinia, Klebsiella, Citrobacter*, or a *Pseudomonas* polypeptide. In a particular embodiment, the polypeptide is derived from *Proteobacteria*, such as *Gammaproteobacteria*, for example *Enterobacteriales*, such as Enterobacteriaceae.

In a particular aspect, the polypeptide derived from Enterobacteriaceae is a *Citrobacter* polypeptide, such as a *Citrobacter amalonaticus, Citrobacter braakii, Citrobacter farmeri, Citrobacter freundii, Citrobacter gillenii, Citrobacter intermedius, Citrobacter koseri, Citrobacter murliniae, Citrobacter rodentium, Citrobacter sedlakii, Citrobacter werkmanii, Citrobacter youngae*, or *Citrobacter* species polypeptide.

In a more preferred aspect, the polypeptide is a *Citrobacter gillenii* polypeptide, and most preferably a *Citrobacter gillenii* DSM 13694 polypeptide, e.g., the polypeptide of SEQ ID NO: 4. The specific strain is publicly available from the Deutsche Sammlung von Mlkroorganismen and Zellkulturen (DSM).

In another more preferred aspect, the polypeptide is a *Citrobacter amalonaticus* polypeptide, and most preferably a *Citrobacter amalonaticus* ATCC 25405 or a *Citrobacter amalonaticus* ATCC 25407 polypeptide, e.g., the polypeptide of SEQ ID NO: 6. These specific strains are publicly available from the American Type Culture Collection, ATCC.

A polypeptide of the present invention may also be a fungal polypeptide, such as a yeast polypeptide or a filamentous fungal polypeptide.

Strains of the above microorganisms are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encodes a polypeptide of the present invention. In a preferred aspect, the nucleotide sequence is set forth in SEQ ID NO: 1, 3, or 5. In another preferred aspect, the nucleotide sequence is the mature polypeptide coding regions of SEQ ID NO: 1, 3, or 5. The present invention also encompasses nucleotide sequences which encode polypeptides having the amino acid sequence of SEQ ID NO: 2, 4, or 6, or the mature polypeptides of any of these, which differ from SEQ ID NO: 1, 3, and 5, respectively, by virtue of the degeneracy of the genetic code. The present invention also relates to subsequences of SEQ ID NO: 1, 3, and 5, which encode fragments of SEQ ID NO: 2, 4, or 6, respectively, that have phytase activity.

The present invention also relates to mutant polynucleotides comprising at least one mutation in the mature polypeptide coding sequence of SEQ ID NO: 1, 3, or 5, in which the mutant nucleotide sequence encodes a polypeptide which consists of amino acids 1 to 409 of SEQ ID NO: 2, or 4, or consists of amino acids 1 to 414 of SEQ ID NO: 6, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Citrobacter*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1, 3, or 5 (i.e., nucleotides 67 to 1293, 67 to 1296, and 67 to 1308, respectively) of at least 75%, and which encode a polypeptide having phytase activity. In particular embodiments, the degree of identity is at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In alternative embodiments, the degree of identity is at least 61%, or at least 62%, 64%, 65%, 66%, 67%, 68%, 69%, 70%, 71%, 72%, 73%, or at least 74%.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH-optimum, or the like. The variant sequence may be constructed on the basis of the nucleotide sequence presented as the polypeptide encoding region of SEQ ID NO: 1, 3 or 5, e.g., a subsequence thereof, and/or by introduction of nucleotide substitutions which do not give rise to another amino acid sequence of the polypeptide encoded by the nucleotide sequence, but which correspond to the codon usage of the host organism intended for production of the polypeptide, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for phytase activity to identify amino acid residues that are critical to the activity of the molecule. Sites of substrate-polypeptide interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under medium stringency conditions, more preferably medium-high stringency conditions, even more preferably high stringency conditions, and most preferably very high stringency conditions with (i) nucleotides 67 to 1293 of SEQ ID NO: 1, nucleotides 67 to 1296 of SEQ ID NO: 3, or nucleotides 67 to 1308 of SEQ ID NO: 5; (ii) the mature polypeptide encoding parts of SEQ ID NO: 1, 3, or 5; and/or (iii) a complementary strand of any one of (i), and/or (ii); or allelic variants and subsequences thereof (Sambrook et al., 1989, supra), as defined herein. In alternative embodiments the hybridization is conducted under very low, or low, stringency conditions.

The present invention also relates to isolated polynucleotides obtained, or obtainable, by (a) hybridizing a population of DNA under very low, low, medium, medium-high, high, or very high stringency conditions with (i) nucleotides 67 to 1293 of SEQ ID NO: 1, nucleotides 67 to 1296 of SEQ ID NO: 3, or nucleotides 67 to 1308 of SEQ ID NO: 5; (ii) the mature polypeptide encoding part of SEQ ID NO: 1, 3, or 5; and/or (iii) a complementary strand of any one of (i), and/or (ii); and (b) isolating the hybridizing polynucleotide, which encodes a polypeptide having phytase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), *Saccharomyces cerevisiae* 3-phosphoglycerate kinase, and *Pichia pastoris* alcohol oxidase (AOX1). Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra, and by Xiong et al., 2005, *Journal of Applied Microbiology* 98: 418-428.

In a preferred aspect, the signal peptide coding region is nucleotides 1 to 66 of SEQ ID NO: 1, 3, or 5, which encode amino acids 1 to 22 of SEQ ID NO: 2, 4, and 6, respectively.

The control sequence may also be a propeptide coding region that codes for an amino acid sequence positioned at the amino terminus of a polypeptide. The resultant polypeptide is known as a propolypeptide or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other *Bacilli*, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyl-transferase (EC 2.7.7.12), or UDP-galactose epimerase (EC 5.1.3.2). Also a xylose isomerase gene such as xylA, of *Bacilli* can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5′-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus,* or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Pichia pastoris, Pichia methanolica, Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola Ian uginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Citrobacter*, and more preferably *Citrobacter gillenii* or *Citrobacter amalonaticus*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 1, 3, or 5, wherein the mutant nucleotide sequence encodes a polypeptide which consists of amino acids 1 to 409 of SEQ ID NO: 2 or 4, or consists of amino acids 1 to 414 of SEQ ID NO: 6, respectively, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a polypeptide product, or disappearance of an polypeptide substrate. For example, a polypeptide assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989). A typical purification scheme may include centrifugation, germ filtration, ammonium sulphate precipitation (using, e.g., 80% ammonium sulphate saturation), centrifugation, re-suspension of pellets in buffer A (e.g., 50 mM sodium acetate, 1.5 M ammonium sulphate pH 4.5), filtration, hydrophobic interaction chromatography (Phenyl Toyopearl, loading with buffer A, eluting with buffer B (50 mM sodium acetate pH 4.5)), and cation exchange chromatography (SP-sepharose, loading with 10 mM sodium citrate pH 4.0, eluting with a linear salt gradient (10 mM sodium citrate pH 4.0+1 M NaCl)).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al., 2000, *PNAS*, 97(4): 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, triticale (stabilized hybrid of wheat (*Triticum*) and rye (*Secale*), and maize (corn). Examples of dicot plants are tobacco, legumes, such as sunflower (*Helianthus*), cotton (*Gossypium*), lupins, potato, sugar beet, pea, bean and soybean, and cruciferous plants (family Brassicaceae), such as cauliflower, rape seed, and the closely related model organism *Arabidopsis thaliana*. Low-phytate plants as described, e.g., in U.S. Pat. Nos. 5,689,054 and 6,111,168 are examples of engineered plants.

Examples of plant parts are stem, callus, leaves, root, fruits, seeds, and tubers, as well as the individual tissues comprising these parts, e.g., epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, *Plant Physiology* 86: 506.

For constitutive expression, the following promoters may be used: The 35S-CaMV promoter (Franck et al., 1980, *Cell* 21: 285-294), the maize ubiquitin 1 (Christensen A H, Sharrock R A and Quail, 1992, Maize polyubiquitin genes: structure, thermal perturbation of expression and transcript splicing, and promoter activity following transfer to protoplasts by electroporation), or the rice actin 1 promoter (*Plant Mol. Biol.* 18: 675-689.; Zhang et al., 1991, Analysis of rice Act1 5' region activity in transgenic rice plants, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought or alterations in salinity or inducible by exogenously applied substances that activate the promoter, e.g., ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al. referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using, e.g., co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Transgenic Animals

The present invention also relates to a transgenic, non-human animal and products or elements thereof, examples of which are body fluids such as milk and blood, organs, flesh, and animal cells. Techniques for expressing proteins, e.g., in mammalian cells, are known in the art, see, e.g., the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having phytase activity of the present invention so as to express and produce the polypeptide. The polypeptide may be recovered from the animal, e.g., from the milk of female animals, or the polypeptide may be expressed to the benefit of the animal itself, e.g., to assist the animal's digestion. Examples of animals are mentioned below in the section headed Animal Feed.

To produce a transgenic animal with a view to recovering the polypeptide from the milk of the animal, a gene encoding the polypeptide may be inserted into the fertilized eggs of an animal in question, e.g., by use of a transgene expression vector which comprises a suitable milk protein promoter, and the gene encoding the polypeptide. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see, e.g., Meade et al. (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the polypeptide, the transgene may be operably linked to a first regulatory sequence for salivary gland specific expression of the polypeptide, as disclosed in WO 00/064247.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.a. the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e., the weight of ingested feed relative to weight gain) of the animal may be improved.

Furthermore, the polypeptide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goats, horses, and cattle, e.g., beef cattle, cows, and young calves. In a particular embodiment, the animal is a non-ruminant animal. Non-ruminant animals include monogastric animals, e.g., pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may, e.g., include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e., in the form of animal feed additives, such as the so-called pre-mixes for animal feed.

In a further aspect the present invention relates to compositions for use in animal feed, such as animal feed, and animal feed additives, e.g., premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g., carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

In a particularly preferred embodiment, the phytase of the invention having a relatively low pH-optimum is combined with at least one phytase having a higher pH-optimum. Preferred examples of phytases of higher pH-optimum are *Bacillus* phytases, such as the phytases from *Bacillus licheniformis* and *Bacillus subtilis*, as well as derivatives, variants, or fragments thereof having phytase activity.

The phytase of the invention may also be combined with other phytases, for example ascomycete phytases such as *Aspergillus* phytases, for example derived from *Aspergillus ficuum*, *Aspergillus niger*, or *Aspergillus awamori*; or basidiomycete phytases, for example derived from *Peniophora lycii*, *Agrocybe pediades*, *Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

The above-mentioned ascomycete and basidiomycete phytases, in particular the RONOZYME P phytase derived from *Peniophora lycii* as well as derivatives, variants, and fragments thereof, may also be combined with *Bacillus* phytases, in particular the *B. licheniformis* phytase as well as with a derivative, fragment or variant thereof, in particular for animal feed purposes.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus* and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can, e.g., be manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 5-30 mg polypeptide protein per kg animal diet.

The phytase of the invention should of course be applied in an effective amount, i.e., in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Signal Peptide

The present invention also relates to nucleic acid constructs comprising a gene encoding a protein operably linked to a first nucleotide sequence consisting of nucleotides 1 to 66 of SEQ ID NO: 1, 3, or 5, encoding a signal peptide consisting of amino acids 1 to 22 of SEQ ID NO: 2, 4 or 6, respectively, wherein the gene is foreign to the first nucleotide sequences.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The first nucleotide sequences may be operably linked to foreign genes individually with other control sequences or in combination with other control sequences. Such other control sequences are described supra.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, polypeptide, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic polypeptide, peroxidase, phytase, polyphenoloxidase, proteolytic polypeptide, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Example 1

Cloning of a *Citrobacter gillenii* Phytase

A multiple alignment was made of the following acid histidine phosphatases: appA *Escherichia coli* (SPTREMBL:

Q8GN88), phyk *Klebsiella terrigena* (SPTREMBL: Q7WSY1), and ypo1648 *Yersinia pestis* CO92 (SPTREMBL:Q8ZFP6). Two degenerate oligonucleotide primers were designed on the basis of consensus sequences:

```
                                (SEQ ID NO: 7, forward primer)
    5'-CGC GTG GTG ATT GTG TCC MGN CAY GGN GT-3'

(SEQ ID NO: 8, reverse primer)
    5'-C CAG GTT GGT ATC ATG GCC NGC DAT RAA-3'.
```

The primers were used for PCR screening of a number of bacterial species at annealing temperatures of 45, 48 and 50° C.

A partial phytase gene in the form of a 900 bp DNA fragment was identified in *Citrobacter gillenii* DSM 13694.

The PCR fragment was cloned into the pEZSeq blunt cloning kit (catalogue no. 40501-1 from Lucigen Corporation, 2120 West Greenview Dr., Ste 9, Middleton, Wis. 53562, US). First, the PCR fragment was treated with the PCRTerminator End Repair Kit (part of the pEZSeq blunt cloning kit), which contains a mixture of enzyme activities that has been optimized to create blunt, 5'-phosphorylated ends on any type of PCR product. After cloning into the pEZSeq vector, the clone was sequenced using two specific vector primers. By translation of the nucleotide sequences, it was confirmed that the cloned DNA fragment was part of a phytase gene.

For obtaining the full length nucleotide sequence of the gene the DNA Walking SpeedUp Kit (DWSK-V102 from Seegene, Inc., 2nd Fl., Myungji Bldg., 142-21, Samsungdong, Kangnam-gu, Seoul, 135-090, Korea) was used, which is designed to capture unknown target sites. For this purpose, 4 specific oligonucleotides were designed and used with the kit.

```
                                         (SEQ ID NO: 9)
    TSP1N:  5'-AGACTTCCGCCAGCCCG-3'

(SEQ ID NO: 10)
    TSP1C:  5'-AAGCAGCTGGGCAGTCTGC-3'

(SEQ ID NO: 11)
    TSP2N:  5'-AAGCGGCGTGAACTTTGTCGG-3'

(SEQ ID NO: 12)
    TSP2C:  5'-ATGGGGACTGGCTTCAACCCTG-3'
```

The full length nucleotide sequence encoding the phytase from *Citrobacter gillenii* DSM 13694 is shown in the sequence listing as SEQ ID NO: 3, and the corresponding encoded amino acid sequence has SEQ ID NO: 4. The first 22 amino acids of SEQ ID NOs: 2 and 4 are expected to be a signal peptide (predicted by Signal P V3.0). SEQ ID NO: 1 is a variant of SEQ ID NO: 3 which comprises the following 13 substitutions: T99G, C102G, C105T, C108G, A109T, G110C, T111C, T117C, C975T, A989C, T991(-), C992(-), A1005(-). SEQ ID NO: 4 is a variant of SEQ ID NO: 2 which comprises the following 5 substitutions: N330T, I331K, S332R, A334(-), L335I.

The *Citrobacter gillenii* DSM 13694 phytase gene was cloned into the pET-30a(+) *E. coli* expression vector without fusion tags (catalogue no. 69909 from Novagen, commercially available from Bie & Berntsen A/S, 7 Sandbaekvej, DK-2610 Roedovre, Denmark). In this system, the expression of the gene is induced by providing a source of T7 RNA polymerase in the *E. coli* BL21star(DE)pLysS host strain (catalogue no. 69388 from Novagen, commercially available from Bie & Berntsen) which contains a chromosomal copy of the T7 RNA polymerase gene under the control of the lacUV5 promoter. The induction of the target gene was performed by adding lactose to the media. Lactose will bind to the repressor and induce its dissociation from the operator, permitting transcription from the promoter.

For expression of the phytase gene, a single colony of the transformed *E. coli* strain was transferred into an inoculum culture in non-inducing media (containing glucose as the sole carbon source) that does not permit expression of the T7 RNA polymerase. As a negative control *E. coli* (BL21star(DE) pLysS) containing an empty pET-30(+) vector was used. A small aliquot (approximately 150 microliters) of the inoculum culture was transferred into flasks containing lactose as the sole carbon source. The induction culture was grown overnight with shaking at 300 rpm at 37° C.

The cells were harvested by centrifugation and 15 microliter aliquots of the supernatant was analyzed by SDS-PAGE. As a molecular weight (MW) marker 10 microliters of the Precision Plus protein standard (catalogue no. 161-0363, commercially available from Bio-Rad Laboratories Headquarters, 1000 Alfred Nobel Drive, Hercules, Calif. 94547, US). A distinct band of MW of approximately 50 kDa was identified in the supernatant from the recombinant *E. coli* strain, but not in the negative control.

The harvested cell pellet was lysed and the soluble intracellular fraction was also analyzed by SDS-PAGE as described above. Also here a band at MW 50 kDa appeared.

This is evidence that the recombinant phytase protein is partially secreted to the media. However, a pool of the enzyme still remains in the intracellular fraction.

The phytase activity of the supernatant and the intracellular fraction was confirmed by use of the assay of Example 4.

Example 2

Preparation of *Citrobacter gillenii* Phytase Preparation

*Citrobacter gillenii* DSM 13694 was grown overnight with shaking (225 rpm) at 30° C. in LB medium (25 g of LB Bouillon, Merck 0285, ion-exchanged water ad 1000 ml) with addition of 0.1% (w/w) sodium phytate. The cells were harvested by centrifugation (4000 rpm, 60 min) and the supernatant discarded. The cell pellet was re-suspended in two volumes of distilled water with 100 mg/ml lysozyme and lysed by overnight incubation at 37° C. The lysed cells were centrifuged (4000 rpm, 2 h) and the supernatant saved and used for acid stability analysis.

Example 3

Acid Stability of the *Citrobacter gillenii* Phytase 50 microliters of the lysate obtained in Example 2 was mixed with 50 microliters of 100 mM buffers with pH values of 2.2, 3.0 (glycine/hydrochloric acid) and 7.0 (HEPES) respectively. The samples were incubated over night at 37° C. and analysed for residual phytase activity using the analytical procedure described in Example 4. The residual phytase activity, expressed as the optical density, is shown in Table 1 below. Furthermore, the activity is calculated in percent relative to the residual activity at pH 7.

TABLE 1

| Strain: | Residual Activity [OD] after incubation at pH: | | | | | |
|---|---|---|---|---|---|---|
| | pH 2.2 | pH 2.2 - relative to pH 7.0 | pH 3.0 | pH 3.0 - relative to pH 7.0 | pH 7.0 | pH 7.0 - relative to pH 7.0 |
| *Citrobacter gillenii* DSM13694 | 0.07 | 81 | 0.10 | 116 | 0.09 | 100 |

Example 4

Phytase Assay

The assay is based on determination of soluble phosphate by complexation with molybdate/iron and photometric measurement of the blue color in microtiter plates.

The substrate is 0.5 mM Na-phytate (Sigma, P-8810) dissolved in 0.1 M acetate-buffer, pH=5.5. In a particular embodiment the substrate concentration is 5 mM.

The color reagent is prepared as follows: 1% Ammoniummolybdat (Merck 1181, $(NH_4)_6Mo_7O_{24}$, $4H_2O$) is dissolved in 3.2% sulfuric acid (Merck 731). 1.1 g ferrosulfate (Merck 3965) is dissolved in 15 ml of the above molybdate reagent and 10 ml of 0.5 M sulfuric acid is added. Is freshly prepared every day, and stored in the dark.

Blind: 20 ul sample, 100 ul substrate and 120 ul color reagent is mixed, incubated 5 min at 37° C. and $OD_{Blind}$ measured at 750 nm.

Sample: 20 ul sample, 100 ul substrate is mixed, incubated 30 min at 37° C., 120 ul color reagent is added, incubated 5 min at 37° C., and $OD_{sample}$ is measured at 750 nm.

$$OD = OD_{sample} - OD_{Blind}.$$

Example 5

Cloning of *Citrobacter amalonaticus* Phytases

A multiple alignment was made of the following acid histidine phosphatases: appA *Escherichia coli* (SPTREMBL: Q8GN88), phyk *Klebsiella terrigena* (SPTREMBL: Q7WSY1), and ypo1648 *Yersinia pestis* CO92 (SPTREMBL:Q8ZFP6). Two degenerate oligonucleotide primers were designed on the basis of consensus sequences:

```
                               (SEQ ID NO: 13, forward primer)
5'-CGC GTG GTG ATT GTG TCC MGN CAY GGN GT-3'

(SEQ ID NO: 14, reverse primer)
5'-C CAG GTT GGT ATC ATG GCC NGC DAT RAA-3'.
```

The primers were used for PCR screening of a number of bacterial species at annealing temperatures of 45, 48 and 50° C.

Partial phytase genes in the form of 900 bp DNA fragments were identified in *Citrobacter amalonaticus* ATCC 25405 and *Citrobacter amalonaticus* ATCC 25407.

The PCR fragments were cloned into the pEZSeq blunt cloning kit (catalogue no. 40501-1 from Lucigen Corporation, 2120 West Greenview Dr., Ste 9, Middleton, Wis. 53562, US). First, the PCR fragments were treated with the PCRTerminator End Repair Kit (part of the pEZSeq blunt cloning kit), which contains a mixture of polypeptide activities that has been optimized to create blunt, 5'-phosphorylated ends on any type of PCR product. After cloning into the pEZSeq vector, the clones were sequenced using two specific vector primers. By translation of the nucleotide sequences, it was confirmed that the cloned DNA fragments were part of phytase genes.

For obtaining the full length nucleotide sequence of the genes the DNA Walking SpeedUp Kit (DWSK-V102 from Seegene, Inc., 2nd Fl., Myungji Bldg., 142-21, Samsungdong, Kangnam-gu, Seoul, 135-090, Korea) was used, which is designed to capture unknown target sites. For this purpose, 4 specific oligonucleotides were designed and used with the kit.

For example, for obtaining the N-terminal and C-terminal sequences of the phytase gene from *Citrobacter amalonaticus* ATCC 25407, oligonucleotides TSP1N/TSP2N and TSP1C/TSP2C were used:

```
                                        (SEQ ID NO: 15)
TSP1N:  5'-TTT ACG AGT GCG CTG ATC GG-3'

(SEQ ID NO: 16)
TSP2N:  5'-ATA ACT GCC ACC TGT TCT GGT GAC G-3'

(SEQ ID NO: 17)
TSP1C:  5'-ACT CAG GGT TTC TGC GGA TAC C-3'

(SEQ ID NO: 18)
TSP2C:  5'-AAT GCC AGA GGT TGC GTG GGG-3'
```

The full length nucleotide sequence encoding the phytase from *Citrobacter amalonaticus* ATCC 25407 is shown in the sequence listing as SEQ ID NO: 5, and the corresponding encoded amino acid sequence has SEQ ID NO: 6. The first 22 amino acids of SEQ ID NO: 6 are expected to be a signal peptide (predicted by Signal P V3.0). The phytase from *Citrobacter amalonaticus* ATCC 25405 has precisely the same amino acid sequence as shown in SEQ ID NO: 6, and the corresponding nucleotide sequence differs by only three nucleotides from SEQ ID NO: 5, viz. T78C, C118T, and T120G, all of which are silent in the sense that they do not give rise to any different amino acid.

The *Citrobacter amalonaticus* ATCC 25407 phytase gene was cloned into the pET-30a(+)*E. coli* expression vector without fusion tags (catalogue no. 69909 from Novagen, commercially available from Bie & Berntsen A/S, 7 Sandbaekvej, DK-2610 Roedovre, Denmark). In this system, the expression of the gene is induced by providing a source of T7 RNA polymerase in the *E. coli* BL21star(DE)pLysS host strain (catalogue no. 69388 from Novagen, commercially available from Bie & Berntsen) which contains a chromosomal copy of the T7 RNA polymerase gene under the control of the lacUV5 promoter. The induction of the target gene was performed by adding lactose to the media. Lactose will bind to the repressor and induce its dissociation from the operator, permitting transcription from the promoter.

For expression of the phytase gene, a single colony of the transformed *E. coli* strain was transferred into an inoculum culture in non-inducing media (containing glucose as the sole carbon source) that does not permit expression of the T7 RNA polymerase. As a negative control *E. coli* (BL21star(DE) pLysS) containing an empty pET-30(+) vector was used. A small aliquot (approximately 150 micro liter) of the inoculum culture was transferred into flasks containing lactose as the sole carbon source. The induction culture was grown overnight with shaking at 300 rpm at 37° C.

The cells were harvested by centrifugation and 15 micro liter aliquots of the supernatant was analyzed by SDS-PAGE. As a molecular weight (MW) marker 10 microliters of the Precision Plus protein standard (catalogue no. 161-0363, commercially available from Bio-Rad Laboratories Headquarters, 1000 Alfred Nobel Drive, Hercules, Calif. 94547, US). A distinct band of MW of approximately 50 kDa was identified in the supernatant from the recombinant *E. coli* strain, but not in the negative control.

The harvested cell pellet was lysed and the soluble intracellular fraction was also analysed by SDS-PAGE as described above. Also here a band at MW 50 kDa appeared.

This is evidence that the recombinant phytase protein is partially secreted to the media. However, a pool of the polypeptide still remains in the intracellular fraction.

The phytase activity of the supernatant and the intracellular fraction was confirmed by use of the assay of Example 4.

Example 6

Preparation of a *Citrobacter amalonaticus* Phytase Preparation

*Citrobacter amalonaticus* ATCC 25405 was grown overnight with shaking (225 rpm) at 30° C. in LB medium (25 g of LB Bouillon, Merck 0285, ion-exchanged water ad 1000 ml) with addition of 0.1% (w/w) sodium phytate. The cells were harvested by centrifugation (4000 rpm, 60 min) and the supernatant discarded. The cell pellet was re-suspended in two volumes of distilled water with 100 mg/ml lysozyme and lysed by overnight incubation at 37° C. The lysed cells were centrifuged (4000 rpm, 2 h) and the supernatant saved and used for acid stability analysis.

Example 7

Acid Stability of the *Citrobacter amalonaticus* Phytase 50 microliters of the lysate obtained in Example 2 was mixed with 50 micro liter of 100 mM buffers with pH values of 2.2, 3.0 (glycine/hydrochloric acid) and 7.0 (HEPES) respectively. The samples were incubated over night at 37° C. and analyzed for residual phytase activity using the analytical procedure described in Example 4. The residual phytase activity, expressed as the optical density, is shown in Table 1 below. Furthermore, the activity is calculated in percent relative to the residual activity at pH 7.

TABLE 1

| | Residual Activity [OD] after incubation at pH: | | | | | |
|---|---|---|---|---|---|---|
| Strain: | pH 2.2 | pH 2.2 - relative to pH 7.0 | pH 3.0 | pH 3.0 - relative to pH 7.0 | pH 7.0 | pH 7.0 - relative to pH 7.0 |
| *Citrobacter amalonaticus* ATCC 25405 | 0.12 | 78 | 0.14 | 100 | 0.14 | 100 |

Particular Embodiments

The following are additional particular embodiments of the present invention:

I. An isolated polypeptide having phytase activity, selected from the group consisting of: (a) a polypeptide having an amino acid sequence which has at least 72% identity with (i) amino acids 1 to 409 of SEQ ID NO: 2, (ii) the mature polypeptide part of SEQ ID NO: 2, (iii) amino acids 1 to 410 of SEQ ID NO: 4, and/or (iv) the mature polypeptide part of SEQ ID NO: 4; (b) a polypeptide which is encoded by a polynucleotide which hybridizes under at least medium stringency conditions with (i) nucleotides 67 to 1293 of SEQ ID NO: 1, (ii) the mature polypeptide encoding part of SEQ ID NO: 1, nucleotides 67 to 1296 of SEQ ID NO: 3, the mature polypeptide encoding part of SEQ ID NO: 3, and/or (v) a complementary strand of any one of (i), (ii), (iii), or (iv); (c) a variant of any one of the polypeptides of (a)(i)-(a)(iv), comprising a conservative substitution, deletion, and/or insertion of one or more amino acids; and (d) a fragment of any one of the polypeptides of (a)(i)-(a)(iv).

II. An isolated polynucleotide comprising a nucleotide sequence which encodes the polypeptide of I.

III. An isolated polynucleotide encoding a polypeptide having phytase activity, selected from the group consisting of: (a) a polynucleotide encoding a polypeptide having an amino acid sequence which has at least 72% identity with amino acids 1 to 409 of SEQ ID NO: 2, or with amino acids 1 to 410 of SEQ ID NO: 4; (b) a polynucleotide having at least 72% identity with nucleotides 67 to 1293 of SEQ ID NO: 1, or with nucleotides 67 to 1296 of SEQ ID NO: 3; and (c) a polynucleotide which hybridizes under at least medium stringency conditions with (i) nucleotides 67 to 1293 of SEQ ID NO: 1, (ii) the mature polypeptide encoding part of SEQ ID NO: 1, (iii) nucleotides 67 to 1296 of SEQ ID NO: 3, (iv) the mature polypeptide encoding part of SEQ ID NO: 3, and/or (v) a complementary strand of any one of (i), (ii), (iii), or (iv).

IV. The isolated polynucleotide of any one of II and III, having at least one mutation in the mature polypeptide coding sequence of SEQ ID NO: 1 or SEQ ID NO: 3, in which the mutant nucleotide sequence encodes a polypeptide comprising amino acids 1 to 409 of SEQ ID NO: 2, or amino acids 1 to 410 of SEQ ID NO: 4.

V. A nucleic acid construct comprising the polynucleotide of any one of II-IV operably linked to one or more control sequences that direct the production of the polypeptide in an expression host.

VI. A recombinant expression vector comprising the nucleic acid construct of V.

VII. A recombinant host cell comprising the nucleic acid construct of V.

VIII. A method for producing the polypeptide of I comprising (a) cultivating a cell, which in its wild-type form is capable of producing the polypeptide, under conditions conducive for production of the polypeptide; and (b) recovering the polypeptide.

IX. A method for producing the polypeptide of I comprising (a) cultivating a recombinant host cell comprising a nucleic acid construct comprising a nucleotide sequence encoding the polypeptide under conditions conducive for production of the polypeptide; and (b) recovering the polypeptide.

X. A transgenic plant, plant part or plant cell, which has been transformed with a polynucleotide encoding the polypeptide of I.

XI. A transgenic, non-human animal, or products, or elements thereof, being capable of expressing the polypeptide of I.

XII. Use of at least one polypeptide of I in animal feed.

XIII. Use of at least one polypeptide of I in the preparation of a composition for use in animal feed.

XIV. A method for improving the nutritional value of an animal feed, wherein at least one polypeptide of I is added to the feed.

XV. An animal feed additive comprising (a) at least one polypeptide of claim 1; and (b) at least one fat soluble vitamin, (c) at least one water soluble vitamin, and/or (d) at least one trace mineral.

XVI. The animal feed additive of XV, which further comprises at least one amylase, at least one additional phytase, at least one xylanase, at least one galactanase, at least one alpha-galactosidase, at least one protease, at least one phospholipase, and/or at least one beta-glucanase.

XVII. The animal feed additive of XVI, wherein the additional phytase has a pH-optimum which is higher than the pH-optimum of the polypeptide having the amino acid sequence of amino acids 1 to 409 of SEQ ID NO: 2, or amino acids 1 to 410 of SEQ ID NO: 4.

XVIII. An animal feed composition having a crude protein content of 50 to 800 g/kg and comprising at least one polypeptide of I.

XIX. An isolated polypeptide having phytase activity, selected from the group consisting of: (a) a polypeptide having an amino acid sequence which has at least 70% identity with (i) amino acids 1 to 414 of SEQ ID NO: 6, and/or (ii) the mature polypeptide part of SEQ ID NO: 6; (b) a polypeptide which is encoded by a polynucleotide which hybridizes under at least medium stringency conditions with (i) nucleotides 67 to 1308 of SEQ ID NO: 5 (ii) the mature polypeptide encoding part of SEQ ID NO: 5, and/or (iii) a complementary strand of any one of (i), (ii), or (iii); (c) a variant of any one of the polypeptides of (a)(i)-(a)(ii), comprising a conservative substitution, deletion, and/or insertion of one or more amino acids; and (d) a fragment of any one of the polypeptides of (a)(i)-(a)(ii).

XX. An isolated polynucleotide comprising a nucleotide sequence which encodes the polypeptide of XIX.

XXI. An isolated polynucleotide encoding a polypeptide having phytase activity, selected from the group consisting of: (a) a polynucleotide encoding a polypeptide having an amino acid sequence which has at least 70% identity with amino acids 1 to 414 of SEQ ID NO: 6; (b) a polynucleotide having at least 71% identity with nucleotides 67 to 1308 of SEQ ID NO: 5; and (c) a polynucleotide which hybridizes under at least medium stringency conditions with (i) nucleotides 67 to 1308 of SEQ ID NO: 5, (ii) the mature polypeptide encoding part of SEQ ID NO: 5, and/or (iii) a complementary strand of any one of (i), (ii), or (iii).

XXII. The isolated polynucleotide of any one of XXII and XXIII, having at least one mutation in the mature polypeptide coding sequence of SEQ ID NO: 5, in which the mutant nucleotide sequence encodes a polypeptide comprising amino acids 1 to 414 of SEQ ID NO: 6.

XXIII. A nucleic acid construct comprising the polynucleotide of any one of XXII-XXIV operably linked to one or more control sequences that direct the production of the polypeptide in an expression host.

XXIV. A recombinant expression vector comprising the nucleic acid construct of XXIII.

XXV. A recombinant host cell comprising the nucleic acid construct of XXIII.

XXVI. A method for producing the polypeptide of XIX, comprising (a) cultivating a cell, which in its wild-type form is capable of producing the polypeptide, under conditions conducive for production of the polypeptide; and (b) recovering the polypeptide.

XXVII. A method for producing the polypeptide of XIX comprising (a) cultivating a recombinant host cell comprising a nucleic acid construct comprising a nucleotide sequence encoding the polypeptide under conditions conducive for production of the polypeptide; and (b) recovering the polypeptide.

XXVIII. A transgenic plant, plant part or plant cell, which has been transformed with a polynucleotide encoding the polypeptide of XIX.

XXIX. A transgenic, non-human animal, or products, or elements thereof, being capable of expressing the polypeptide of XIX.

XXX. Use of at least one polypeptide of XIX in animal feed.

XXXI. Use of at least one polypeptide of XIX in the preparation of a composition for use in animal feed.

XXXII. A method for improving the nutritional value of an animal feed, wherein at least one polypeptide of XIX is added to the feed.

XXXIII. An animal feed additive comprising (a) at least one polypeptide of XIX; and (b) at least one fat soluble vitamin, (c) at least one water soluble vitamin, and/or (d) at least one trace mineral.

XXXIV. The animal feed additive of XXXIII, which further comprises at least one amylase, at least one additional phytase, at least one xylanase, at least one galactanase, at least one alpha-galactosidase, at least one protease, at least one phospholipase, and/or at least one beta-glucanase.

XXXV. The animal feed additive of XXXIV, wherein the additional phytase has a pH-optimum which is higher than the pH-optimum of the polypeptide having the amino acid sequence of amino acids 1 to 414 of SEQ ID NO: 6.

XXXVI. An animal feed composition having a crude protein content of 50 to 800 g/kg and comprising at least one polypeptide of XIX.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. An isolated polypeptide having phytase activity, which is selected from the group consisting of:

(a) a polypeptide having at least 95% sequence identity with amino acids 1 to 409 of the polypeptide of SEQ ID NO: 2 and/or amino acids 1 to 410 of SEQ ID NO: 4; and (b) a fragment of the polypeptide of SEQ ID NO: 2 or 4 wherein said fragment has phytase activity.

2. The polypeptide of claim 1, which has at least 95% sequence identity with amino acids 1 to 409 of the polypeptide of SEQ ID NO: 2 and/or amino acids 1 to 410 of SEQ ID NO: 4.

3. The polypeptide of claim 1, which has at least 97% sequence identity with amino acids 1 to 409 of the polypeptide of SEQ ID NO: 2 and/or amino acids 1 to 410 of SEQ ID NO: 4.

4. The polypeptide of claim 1, which has at least 98% sequence identity with amino acids 1 to 409 of the polypeptide of SEQ ID NO: 2 and/or amino acids 1 to 410 of SEQ ID NO: 4.

5. The polypeptide of claim 1, which has at least 99% sequence identity with amino acids 1 to 409 of the polypeptide of SEQ ID NO: 2 and/or amino acids 1 to 410 of SEQ ID NO: 4.

6. The polypeptide of claim 1, which is encoded by a polynucleotide which hybridizes under high stringency conditions with nucleotides 67 to 1293 of the polynucleotide of SEQ ID NO: 1, nucleotides 67 to 1296 of the polynucleotide of SEQ ID NO: 3, and/or either of their full-length complementary strands, wherein the high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC and 0.2% SDS at 65° C.

7. The polypeptide of claim 1, which is encoded by a polynucleotide which hybridizes under very high stringency conditions with nucleotides 67 to 1293 of the polynucleotide of SEQ ID NO: 1, nucleotides 67 to 1296 of the polynucleotide of SEQ ID NO: 3, and/or either of their full-length complementary strands, wherein the very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC and 0.2% SDS at 70° C.

8. The polypeptide of claim 1, wherein the polypeptide is a fragment of the polypeptide of SEQ ID NO: 2 or 4 which has phytase activity.

9. The polypeptide of claim 8, wherein the fragment has at least 350 amino acids.

10. The polypeptide of claim 8, wherein the fragment has at least 380 amino acids.

11. The polypeptide of claim 8, wherein the fragment has at least 400 amino acids.

12. The polypeptide of claim 1, which has the conserved active site motif of Arg-His-Gly-Xaa-Arg-Xaa-Pro (SEQ ID NO: 19) at a position corresponding to positions 16-22 of SEQ ID NO: 6.

13. The polypeptide of claim 1, wherein the polypeptide comprises the sequence of amino acids 1 to 409 of the polypeptide of SEQ ID NO: 2 or amino acids 1 to 410 of SEQ ID NO: 4.

14. An animal feed additive comprising at least one polypeptide of claim 1; and further comprising
(a) at least one fat soluble vitamin,
(b) at least one water soluble vitamin, and/or
(c) at least one trace mineral.

15. The animal feed additive of claim 14, which further comprises at least one amylase, at least one additional phytase, at least one xylanase, at least one galactanase, at least one alpha-galactosidase, at least one protease, at least one phospholipase, and/or at least one beta-glucanase.

16. An animal feed composition having a crude protein content of 50 to 800 g/kg and comprising at least one polypeptide of claim 1.

17. A method for improving the nutritional value of an animal feed, comprising adding at least one polypeptide of claim 1 to the feed.

* * * * *

SEQUENCE LISTING

<160> NUMBER OF SEQ ID NOS: 19

<210> SEQ ID NO 1
<211> LENGTH: 1296
<212> TYPE: DNA
<213> ORGANISM: Artificial sequence
<220> FEATURE:

```
<223> OTHER INFORMATION: Synthetic construct
<220> FEATURE:
<221> NAME/KEY: CDS
<222> LOCATION: (1)..(1293)
<220> FEATURE:
<221> NAME/KEY: mat_peptide
<222> LOCATION: (67)..(1293)

<400> SEQUENCE: 1
```

| | | | | | | | | | | | | | | | | |
|---|---|---|---|---|---|---|---|---|---|---|---|---|---|---|---|---|
| atg | agt | aca | ctg | atc | att | cgt | tta | ttg | ttc | tta | acg | att | ata | ttg | gcc | 48 |
| Met | Ser | Thr | Leu | Ile | Ile | Arg | Leu | Leu | Phe | Leu | Thr | Ile | Ile | Leu | Ala | |
| | | -20 | | | | -15 | | | | -10 | | | | | | |
| cct | gtt | tca | tta | cgc | gcc | gat | gaa | cag | agc | gga | atg | cag | ctt | gag | cgt | 96 |
| Pro | Val | Ser | Leu | Arg | Ala | Asp | Glu | Gln | Ser | Gly | Met | Gln | Leu | Glu | Arg | |
| | -5 | | | | -1 | 1 | | | 5 | | | | | | 10 | |
| gtg | gtg | att | gtg | tcc | cgt | cac | ggc | gtc | agg | gca | ccg | aca | aag | ttc | acg | 144 |
| Val | Val | Ile | Val | Ser | Arg | His | Gly | Val | Arg | Ala | Pro | Thr | Lys | Phe | Thr | |
| | | | | 15 | | | | | 20 | | | | | 25 | | |
| ccg | ctt | atg | cag | caa | gtc | act | ccc | gac | cgc | tgg | ccg | caa | tgg | gac | gtt | 192 |
| Pro | Leu | Met | Gln | Gln | Val | Thr | Pro | Asp | Arg | Trp | Pro | Gln | Trp | Asp | Val | |
| | | | 30 | | | | | 35 | | | | | 40 | | | |
| cct | ctg | ggg | tgg | ttg | act | cct | cgc | ggc | ggg | gca | ctc | att | act | gag | tta | 240 |
| Pro | Leu | Gly | Trp | Leu | Thr | Pro | Arg | Gly | Gly | Ala | Leu | Ile | Thr | Glu | Leu | |
| | | 45 | | | | | 50 | | | | | 55 | | | | |
| gga | cgg | tat | caa | cgt | tta | cgc | ctg | gcg | gac | aaa | ggt | ctg | ctg | gat | aat | 288 |
| Gly | Arg | Tyr | Gln | Arg | Leu | Arg | Leu | Ala | Asp | Lys | Gly | Leu | Leu | Asp | Asn | |
| | 60 | | | | | 65 | | | | | 70 | | | | | |
| aaa | acg | tgt | cca | acg | gca | ggg | cag | gtc | gcg | gtc | att | gcc | gat | agc | gat | 336 |
| Lys | Thr | Cys | Pro | Thr | Ala | Gly | Gln | Val | Ala | Val | Ile | Ala | Asp | Ser | Asp | |
| 75 | | | | | 80 | | | | | 85 | | | | | 90 | |
| caa | cgt | acc | cgt | aaa | acg | ggt | gaa | gca | ttc | ctg | gca | gga | ctg | gct | ccg | 384 |
| Gln | Arg | Thr | Arg | Lys | Thr | Gly | Glu | Ala | Phe | Leu | Ala | Gly | Leu | Ala | Pro | |
| | | | 95 | | | | | 100 | | | | | 105 | | | |
| gaa | tgt | aaa | gta | cag | gtt | tat | tat | caa | caa | gat | aag | tca | aaa | tct | gat | 432 |
| Glu | Cys | Lys | Val | Gln | Val | Tyr | Tyr | Gln | Gln | Asp | Lys | Ser | Lys | Ser | Asp | |
| | | 110 | | | | | 115 | | | | | 120 | | | | |
| ccc | ctt | ttt | aat | ccc | atc | aag | gcg | ggg | cgg | tgt | tcg | ctg | aac | aca | tcg | 480 |
| Pro | Leu | Phe | Asn | Pro | Ile | Lys | Ala | Gly | Arg | Cys | Ser | Leu | Asn | Thr | Ser | |
| | 125 | | | | | 130 | | | | | 135 | | | | | |
| cag | gtg | aaa | gag | gcc | atc | ctg | acc | cgg | gct | ggc | gga | agt | ctt | gat | gag | 528 |
| Gln | Val | Lys | Glu | Ala | Ile | Leu | Thr | Arg | Ala | Gly | Gly | Ser | Leu | Asp | Glu | |
| 140 | | | | | 145 | | | | | 150 | | | | | | |
| tac | acg | cgc | cac | tac | caa | ccc | gca | ttt | caa | gcc | ctg | gaa | cgg | gtg | tta | 576 |
| Tyr | Thr | Arg | His | Tyr | Gln | Pro | Ala | Phe | Gln | Ala | Leu | Glu | Arg | Val | Leu | |
| 155 | | | | 160 | | | | | 165 | | | | | 170 | | |
| aat | ttc | tcc | cag | tca | gaa | aag | tgt | caa | gca | gct | ggg | cag | tct | gca | cag | 624 |
| Asn | Phe | Ser | Gln | Ser | Glu | Lys | Cys | Gln | Ala | Ala | Gly | Gln | Ser | Ala | Gln | |
| | | | 175 | | | | | 180 | | | | | 185 | | | |
| tgt | acg | cta | acc | gac | gtc | tta | cct | gct | gaa | ctc | aag | gtc | tct | cca | gaa | 672 |
| Cys | Thr | Leu | Thr | Asp | Val | Leu | Pro | Ala | Glu | Leu | Lys | Val | Ser | Pro | Glu | |
| | | 190 | | | | | 195 | | | | | 200 | | | | |
| aat | ata | tcg | ttg | tca | ggc | tca | tgg | gga | ctg | gct | tca | acc | ctg | acg | gaa | 720 |
| Asn | Ile | Ser | Leu | Ser | Gly | Ser | Trp | Gly | Leu | Ala | Ser | Thr | Leu | Thr | Glu | |
| | 205 | | | | | 210 | | | | | 215 | | | | | |
| atc | ttc | ctg | ctg | caa | caa | gca | caa | ggg | atg | tcg | cag | gtg | gcc | tgg | ggg | 768 |
| Ile | Phe | Leu | Leu | Gln | Gln | Ala | Gln | Gly | Met | Ser | Gln | Val | Ala | Trp | Gly | |
| 220 | | | | | 225 | | | | | 230 | | | | | | |
| cgt | att | cat | ggc | gat | aaa | gaa | tgg | cgt | aca | tta | tta | agt | ctg | cac | aat | 816 |
| Arg | Ile | His | Gly | Asp | Lys | Glu | Trp | Arg | Thr | Leu | Leu | Ser | Leu | His | Asn | |
| 235 | | | | 240 | | | | | 245 | | | | | 250 | | |
| gcg | cag | ttt | gac | ctt | ctg | cag | aaa | acc | ccg | gag | gtt | gcc | cgt | agc | agg | 864 |
| Ala | Gln | Phe | Asp | Leu | Leu | Gln | Lys | Thr | Pro | Glu | Val | Ala | Arg | Ser | Arg | |

```
                    255                 260                 265
gcc aca ccg tta ctt gat ttg ata cgt aca gca ctc gta aca cag ggg    912
Ala Thr Pro Leu Leu Asp Leu Ile Arg Thr Ala Leu Val Thr Gln Gly
        270                 275                 280 gca aca gaa aat aaa tac gca att cag ttg ccc gtc tct ttg ttg ttt    960
Ala Thr Glu Asn Lys Tyr Ala Ile Gln Leu Pro Val Ser Leu Leu Phe
            285                 290                 295 att gcg ggg cat gat acc aat ctt gcc act aag cgg ggc att ggc ctt    1008
Ile Ala Gly His Asp Thr Asn Leu Ala Thr Lys Arg Gly Ile Gly Leu
300                 305                 310 aac gtg ttt ctg ccc ggt cag cca gat aat acg ccg ccg ggt gga gag    1056
Asn Val Phe Leu Pro Gly Gln Pro Asp Asn Thr Pro Pro Gly Gly Glu
315                 320                 325                 330 ttt gtt ttc gaa agg tgg aaa cgg gtc agc gat cat tct gat tgg gtg    1104
Phe Val Phe Glu Arg Trp Lys Arg Val Ser Asp His Ser Asp Trp Val
                335                 340                 345 cag gtt tct ttt atg tat cag aca ttg cag gaa atg cgt gat atg caa    1152
Gln Val Ser Phe Met Tyr Gln Thr Leu Gln Glu Met Arg Asp Met Gln
            350                 355                 360 cct ttg tcg ttg caa tcg cct ccc gga aaa att gtg ctg ccc tta gcg    1200
Pro Leu Ser Leu Gln Ser Pro Pro Gly Lys Ile Val Leu Pro Leu Ala
        365                 370                 375 gcc tgc gat gag aaa aat acg cag gga atg tgc tca tta aaa aat ttt    1248
Ala Cys Asp Glu Lys Asn Thr Gln Gly Met Cys Ser Leu Lys Asn Phe
380                 385                 390 tct gca ctg att gat tcc gtt cgc gtg tcc gaa tgt gct gag aaa taa    1296
Ser Ala Leu Ile Asp Ser Val Arg Val Ser Glu Cys Ala Glu Lys
395                 400                 405

<210> SEQ ID NO 2
<211> LENGTH: 431
<212> TYPE: PRT
<213> ORGANISM: Artificial sequence
<220> FEATURE:
<223> OTHER INFORMATION: Synthetic Construct

<400> SEQUENCE: 2

Met Ser Thr Leu Ile Ile Arg Leu Leu Phe Leu Thr Ile Ile Leu Ala
        -20                 -15                 -10

Pro Val Ser Leu Arg Ala Asp Glu Gln Ser Gly Met Gln Leu Glu Arg
    -5                  -1  1               5                   10

Val Val Ile Val Ser Arg His Gly Val Arg Ala Pro Thr Lys Phe Thr
                15                  20                  25

Pro Leu Met Gln Gln Val Thr Pro Asp Arg Trp Pro Gln Trp Asp Val
                30                  35                  40

Pro Leu Gly Trp Leu Thr Pro Arg Gly Gly Ala Leu Ile Thr Glu Leu
            45                  50                  55

Gly Arg Tyr Gln Arg Leu Arg Leu Ala Asp Lys Gly Leu Leu Asp Asn
        60                  65                  70

Lys Thr Cys Pro Thr Ala Gly Gln Val Ala Val Ile Ala Asp Ser Asp
75                  80                  85                  90

Gln Arg Thr Arg Lys Thr Gly Glu Ala Phe Leu Ala Gly Leu Ala Pro
                95                  100                 105

Glu Cys Lys Val Gln Val Tyr Tyr Gln Gln Asp Lys Ser Lys Ser Asp
            110                 115                 120

Pro Leu Phe Asn Pro Ile Lys Ala Gly Arg Cys Ser Leu Asn Thr Ser
        125                 130                 135

Gln Val Lys Glu Ala Ile Leu Thr Arg Ala Gly Gly Ser Leu Asp Glu
    140                 145                 150
```

```
Tyr Thr Arg His Tyr Gln Pro Ala Phe Gln Ala Leu Glu Arg Val Leu
155                 160                 165                 170

Asn Phe Ser Gln Ser Glu Lys Cys Gln Ala Ala Gly Gln Ser Ala Gln
            175                 180                 185

Cys Thr Leu Thr Asp Val Leu Pro Ala Glu Leu Lys Val Ser Pro Glu
        190                 195                 200

Asn Ile Ser Leu Ser Gly Ser Trp Gly Leu Ala Ser Thr Leu Thr Glu
    205                 210                 215

Ile Phe Leu Leu Gln Gln Ala Gln Gly Met Ser Gln Val Ala Trp Gly
220                 225                 230

Arg Ile His Gly Asp Lys Glu Trp Arg Thr Leu Ser Leu His Asn
235                 240                 245                 250

Ala Gln Phe Asp Leu Leu Gln Lys Thr Pro Glu Val Ala Arg Ser Arg
            255                 260                 265

Ala Thr Pro Leu Leu Asp Leu Ile Arg Thr Ala Leu Val Thr Gln Gly
        270                 275                 280

Ala Thr Glu Asn Lys Tyr Ala Ile Gln Leu Pro Val Ser Leu Leu Phe
    285                 290                 295

Ile Ala Gly His Asp Thr Asn Leu Ala Thr Lys Arg Gly Ile Gly Leu
300                 305                 310

Asn Val Phe Leu Pro Gly Gln Pro Asp Asn Thr Pro Pro Gly Gly Glu
315                 320                 325                 330

Phe Val Phe Glu Arg Trp Lys Arg Val Ser Asp His Ser Asp Trp Val
            335                 340                 345

Gln Val Ser Phe Met Tyr Gln Thr Leu Gln Glu Met Arg Asp Met Gln
        350                 355                 360

Pro Leu Ser Leu Gln Ser Pro Gly Lys Ile Val Leu Pro Leu Ala
    365                 370                 375

Ala Cys Asp Glu Lys Asn Thr Gln Gly Met Cys Ser Leu Lys Asn Phe
380                 385                 390

Ser Ala Leu Ile Asp Ser Val Arg Val Ser Glu Cys Ala Glu Lys
395                 400                 405

<210> SEQ ID NO 3
<211> LENGTH: 1296
<212> TYPE: DNA
<213> ORGANISM: Citrobacter gillenii DSM 13694
<220> FEATURE:
<221> NAME/KEY: CDS
<222> LOCATION: (1)..(1296)
<220> FEATURE:
<221> NAME/KEY: mat_peptide
<222> LOCATION: (67)..(1296)

<400> SEQUENCE: 3 atg agt aca ctg atc att cgt tta ttg ttc tta acg att ata ttg gcc     48
Met Ser Thr Leu Ile Ile Arg Leu Leu Phe Leu Thr Ile Ile Leu Ala
        -20                 -15                 -10 cct gtt tca tta cgc gcc gat gaa cag agc gga atg cag ctt gag cgt     96
Pro Val Ser Leu Arg Ala Asp Glu Gln Ser Gly Met Gln Leu Glu Arg
        -5              -1  1               5                  10 gtt gtc atc gtc agt cgt cat ggc gtc agg gca ccg aca aag ttc acg    144
Val Val Ile Val Ser Arg His Gly Val Arg Ala Pro Thr Lys Phe Thr
                15                  20                  25 ccg ctt atg cag caa gtc act ccc gac cgc tgg ccg caa tgg gac gtt    192
Pro Leu Met Gln Gln Val Thr Pro Asp Arg Trp Pro Gln Trp Asp Val
            30                  35                  40 cct ctg ggg tgg ttg act cct cgc ggc ggg gca ctc att act gag tta    240
```

```
                Pro Leu Gly Trp Leu Thr Pro Arg Gly Gly Ala Leu Ile Thr Glu Leu
                        45                  50                  55 gga cgg tat caa cgt tta cgc ctg gcg gac aaa ggt ctg ctg gat aat         288
Gly Arg Tyr Gln Arg Leu Arg Leu Ala Asp Lys Gly Leu Leu Asp Asn
        60                  65                  70 aaa acg tgt cca acg gca ggg cag gtc gcg gtc att gcc gat agc gat         336
Lys Thr Cys Pro Thr Ala Gly Gln Val Ala Val Ile Ala Asp Ser Asp
75                  80                  85                  90 caa cgt acc cgt aaa acg ggt gaa gca ttc ctg gca gga ctg gct ccg         384
Gln Arg Thr Arg Lys Thr Gly Glu Ala Phe Leu Ala Gly Leu Ala Pro
                95                  100                 105 gaa tgt aaa gta cag gtt tat tat caa caa gat aag tca aaa tct gat         432
Glu Cys Lys Val Gln Val Tyr Tyr Gln Gln Asp Lys Ser Lys Ser Asp
            110                 115                 120 ccc ctt ttt aat ccc atc aag gcg ggg cgg tgt tcg ctg aac aca tcg         480
Pro Leu Phe Asn Pro Ile Lys Ala Gly Arg Cys Ser Leu Asn Thr Ser
        125                 130                 135 cag gtg aaa gag gcc atc ctg acc cgg gct ggc gga agt ctt gat gag         528
Gln Val Lys Glu Ala Ile Leu Thr Arg Ala Gly Gly Ser Leu Asp Glu
    140                 145                 150 tac acg cgc cac tac caa ccc gca ttt caa gcc ctg gaa cgg gtg tta         576
Tyr Thr Arg His Tyr Gln Pro Ala Phe Gln Ala Leu Glu Arg Val Leu
155                 160                 165                 170 aat ttc tcc cag tca gaa aag tgt caa gca gct ggg cag tct gca cag         624
Asn Phe Ser Gln Ser Glu Lys Cys Gln Ala Ala Gly Gln Ser Ala Gln
                175                 180                 185 tgt acg cta acc gac gtc tta cct gct gaa ctc aag gtc tct cca gaa         672
Cys Thr Leu Thr Asp Val Leu Pro Ala Glu Leu Lys Val Ser Pro Glu
            190                 195                 200 aat ata tcg ttg tca ggc tca tgg gga ctg gct tca acc ctg acg gaa         720
Asn Ile Ser Leu Ser Gly Ser Trp Gly Leu Ala Ser Thr Leu Thr Glu
        205                 210                 215 atc ttc ctg ctg caa caa gca caa ggg atg tcg cag gtg gcc tgg ggg         768
Ile Phe Leu Leu Gln Gln Ala Gln Gly Met Ser Gln Val Ala Trp Gly
    220                 225                 230 cgt att cat ggc gat aaa gaa tgg cgt aca tta tta agt ctg cac aat         816
Arg Ile His Gly Asp Lys Glu Trp Arg Thr Leu Leu Ser Leu His Asn
235                 240                 245                 250 gcg cag ttt gac ctt ctg cag aaa acc ccg gag gtt gcc cgt agc agg         864
Ala Gln Phe Asp Leu Leu Gln Lys Thr Pro Glu Val Ala Arg Ser Arg
                255                 260                 265 gcc aca ccg tta ctt gat ttg ata cgt aca gca ctc gta aca cag ggg         912
Ala Thr Pro Leu Leu Asp Leu Ile Arg Thr Ala Leu Val Thr Gln Gly
            270                 275                 280 gca aca gaa aat aaa tac gca att cag ttg ccc gtc tct ttg ttg ttt         960
Ala Thr Glu Asn Lys Tyr Ala Ile Gln Leu Pro Val Ser Leu Leu Phe
        285                 290                 295 att gcg ggg cat gac acc aat ctt gcc aat atc agc ggg gca tta ggc        1008
Ile Ala Gly His Asp Thr Asn Leu Ala Asn Ile Ser Gly Ala Leu Gly
    300                 305                 310 ctt aac gtg ttt ctg ccc ggt cag cca gat aat acg ccg ccg ggt gga        1056
Leu Asn Val Phe Leu Pro Gly Gln Pro Asp Asn Thr Pro Pro Gly Gly
315                 320                 325                 330 gag ttt gtt ttc gaa agg tgg aaa cgg gtc agc gat cat tct gat tgg        1104
Glu Phe Val Phe Glu Arg Trp Lys Arg Val Ser Asp His Ser Asp Trp
                335                 340                 345 gtg cag gtt tct ttt atg tat cag aca ttg cag gaa atg cgt gat atg        1152
Val Gln Val Ser Phe Met Tyr Gln Thr Leu Gln Glu Met Arg Asp Met
            350                 355                 360 caa cct ttg tcg ttg caa tcg cct ccc gga aaa att gtg ctg ccc tta        1200
```

```
Gln Pro Leu Ser Leu Gln Ser Pro Gly Lys Ile Val Pro Leu
        365                 370                 375 gcg gcc tgc gat gag aaa aat acg cag gga atg tgc tca tta aaa aat      1248
Ala Ala Cys Asp Glu Lys Asn Thr Gln Gly Met Cys Ser Leu Lys Asn
        380                 385                 390 ttt tct gca ctg att gat tcc gtt cgc gtg tcc gaa tgt gct gag aaa      1296
Phe Ser Ala Leu Ile Asp Ser Val Arg Val Ser Glu Cys Ala Glu Lys
395                 400                 405                 410
```

<210> SEQ ID NO 4
<211> LENGTH: 432
<212> TYPE: PRT
<213> ORGANISM: Citrobacter gillenii DSM 13694

<400> SEQUENCE: 4

```
Met Ser Thr Leu Ile Ile Arg Leu Leu Phe Leu Thr Ile Ile Leu Ala
        -20                 -15                 -10

Pro Val Ser Leu Arg Ala Asp Glu Gln Ser Gly Met Gln Leu Glu Arg
         -5              -1  1               5                  10

Val Val Ile Val Ser Arg His Gly Val Arg Ala Pro Thr Lys Phe Thr
                15                  20                  25

Pro Leu Met Gln Val Thr Pro Asp Arg Trp Pro Gln Trp Asp Val
                30                  35                  40

Pro Leu Gly Trp Leu Thr Pro Arg Gly Gly Ala Leu Ile Thr Glu Leu
            45                  50                  55

Gly Arg Tyr Gln Arg Leu Arg Leu Ala Asp Lys Gly Leu Leu Asp Asn
    60                  65                  70

Lys Thr Cys Pro Thr Ala Gly Gln Val Ala Val Ile Ala Asp Ser Asp
75                  80                  85                  90

Gln Arg Thr Arg Lys Thr Gly Glu Ala Phe Leu Ala Gly Leu Ala Pro
                95                  100                 105

Glu Cys Lys Val Gln Val Tyr Tyr Gln Gln Asp Lys Ser Lys Ser Asp
            110                 115                 120

Pro Leu Phe Asn Pro Ile Lys Ala Gly Arg Cys Ser Leu Asn Thr Ser
        125                 130                 135

Gln Val Lys Glu Ala Ile Leu Thr Arg Ala Gly Gly Ser Leu Asp Glu
    140                 145                 150

Tyr Thr Arg His Tyr Gln Pro Ala Phe Gln Ala Leu Glu Arg Val Leu
155                 160                 165                 170

Asn Phe Ser Gln Ser Glu Lys Cys Gln Ala Ala Gly Gln Ser Ala Gln
                175                 180                 185

Cys Thr Leu Thr Asp Val Leu Pro Ala Glu Leu Lys Val Ser Pro Glu
            190                 195                 200

Asn Ile Ser Leu Ser Gly Ser Trp Gly Leu Ala Ser Thr Leu Thr Glu
        205                 210                 215

Ile Phe Leu Leu Gln Gln Ala Gln Gly Met Ser Gln Val Ala Trp Gly
    220                 225                 230

Arg Ile His Gly Asp Lys Glu Trp Arg Thr Leu Leu Ser Leu His Asn
235                 240                 245                 250

Ala Gln Phe Asp Leu Leu Gln Lys Thr Pro Glu Val Ala Arg Ser Arg
                255                 260                 265

Ala Thr Pro Leu Leu Asp Leu Ile Arg Thr Ala Leu Val Thr Gln Gly
            270                 275                 280

Ala Thr Glu Asn Lys Tyr Ala Ile Gln Leu Pro Val Ser Leu Leu Phe
        285                 290                 295

Ile Ala Gly His Asp Thr Asn Leu Ala Asn Ile Ser Gly Ala Leu Gly
```

```
                         300                 305                 310
Leu Asn Val Phe Leu Pro Gly Gln Pro Asp Asn Thr Pro Pro Gly Gly
315                 320                 325                 330

Glu Phe Val Phe Glu Arg Trp Lys Arg Val Ser Asp His Ser Asp Trp
                335                 340                 345

Val Gln Val Ser Phe Met Tyr Gln Thr Leu Gln Glu Met Arg Asp Met
                    350                 355                 360

Gln Pro Leu Ser Leu Gln Ser Pro Pro Gly Lys Ile Val Leu Pro Leu
            365                 370                 375

Ala Ala Cys Asp Glu Lys Asn Thr Gln Gly Met Cys Ser Leu Lys Asn
        380                 385                 390

Phe Ser Ala Leu Ile Asp Ser Val Arg Val Ser Glu Cys Ala Glu Lys
395                 400                 405                 410

<210> SEQ ID NO 5
<211> LENGTH: 1311
<212> TYPE: DNA
<213> ORGANISM: Citrobacter amalonaticus ATCC 25407
<220> FEATURE:
<221> NAME/KEY: CDS
<222> LOCATION: (1)..(1308)
<220> FEATURE:
<221> NAME/KEY: mat_peptide
<222> LOCATION: (67)..(1308)

<400> SEQUENCE: 5 atg aat acg cta ctt ttt cga tta ata atg ttt ata ttc atg ttt ggt     48
Met Asn Thr Leu Leu Phe Arg Leu Ile Met Phe Ile Phe Met Phe Gly
        -20                 -15                 -10 tct ttc cca tta cag gcg gaa gtg cca gat gac atg aag ctt gaa cga     96
Ser Phe Pro Leu Gln Ala Glu Val Pro Asp Asp Met Lys Leu Glu Arg
     -5                 -1   1               5                  10 gtt gtg ata gta agt cgc cac ggt gta aga gca cca aca aag ttc acc    144
Val Val Ile Val Ser Arg His Gly Val Arg Ala Pro Thr Lys Phe Thr
                 15                  20                  25 cca ttg atg cag gaa atc aca cct tac cat tgg ccg caa tgg gat gtt    192
Pro Leu Met Gln Glu Ile Thr Pro Tyr His Trp Pro Gln Trp Asp Val
             30                  35                  40 ccc ctg ggc tgg ttg acg gct cgg ggt ggt gag ctc gtc acc gaa atg    240
Pro Leu Gly Trp Leu Thr Ala Arg Gly Gly Glu Leu Val Thr Glu Met
         45                  50                  55 gga cga tat caa caa aaa gta tta atc gat aac ggc gtt ctg gaa agt    288
Gly Arg Tyr Gln Gln Lys Val Leu Ile Asp Asn Gly Val Leu Glu Ser
 60                  65                  70 aat gta tgt ccg tca cca gaa cag gtg gca gtt att gcc gat acc gat    336
Asn Val Cys Pro Ser Pro Glu Gln Val Ala Val Ile Ala Asp Thr Asp
 75                  80                  85                  90 cag cgc act cgt aaa acc ggt gag gca ttt ctg gct gga ttt gcg ccg    384
Gln Arg Thr Arg Lys Thr Gly Glu Ala Phe Leu Ala Gly Phe Ala Pro
                 95                 100                 105 gga tgt aaa aat aag gtt cat tat caa aaa gat cac gat aaa aaa gat    432
Gly Cys Lys Asn Lys Val His Tyr Gln Lys Asp His Asp Lys Lys Asp
            110                 115                 120 cct ctt ttt aat cca gta aaa atg ggg gtg tgc gct ttt aat gta caa    480
Pro Leu Phe Asn Pro Val Lys Met Gly Val Cys Ala Phe Asn Val Gln
        125                 130                 135 aaa act cag gaa gcg att ctg aca cgt gcg gaa gga aac att gaa cgg    528
Lys Thr Gln Glu Ala Ile Leu Thr Arg Ala Glu Gly Asn Ile Glu Arg
    140                 145                 150 tac act cag cgt tat gac tct gca ttc cgt act ctg gaa cag gtt ctc    576
Tyr Thr Gln Arg Tyr Asp Ser Ala Phe Arg Thr Leu Glu Gln Val Leu
```

```
                  155                 160                 165                 170
aat ttc tcc cgg tca gca gca tgc cga tca gca agc cag tct ggt tgc      624
Asn Phe Ser Arg Ser Ala Ala Cys Arg Ser Ala Ser Gln Ser Gly Cys
                175                 180                 185 acg cta cca gga acc tta cct tca gaa ctc agg gtt tct gcg gat acc      672
Thr Leu Pro Gly Thr Leu Pro Ser Glu Leu Arg Val Ser Ala Asp Thr
                190                 195                 200 gtt tcc tta tct ggc gcg tgg agt ctt tct tcc atg ctg acg gaa ata      720
Val Ser Leu Ser Gly Ala Trp Ser Leu Ser Ser Met Leu Thr Glu Ile
                205                 210                 215 ttt cta ttg caa gag gcg cag gga atg cca gag gtt gcg tgg ggg cga      768
Phe Leu Leu Gln Glu Ala Gln Gly Met Pro Glu Val Ala Trp Gly Arg
                220                 225                 230 att cat ggg gag aaa gaa tgg aca gcg tta tta agt ctg cat aat gct      816
Ile His Gly Glu Lys Glu Trp Thr Ala Leu Leu Ser Leu His Asn Ala
235                 240                 245                 250 cag ttt gac ctt ttg caa aga act ccc gaa gtt gcc cgc agc aga gca      864
Gln Phe Asp Leu Leu Gln Arg Thr Pro Glu Val Ala Arg Ser Arg Ala
                255                 260                 265 aca cca tta ctc gat ttg atc agc gaa gca tta gtg agt aat ggg tca      912
Thr Pro Leu Leu Asp Leu Ile Ser Glu Ala Leu Val Ser Asn Gly Ser
                270                 275                 280 aca gaa aat cat tac gga att aaa tta ccc gtc tca tta ttg ttt att      960
Thr Glu Asn His Tyr Gly Ile Lys Leu Pro Val Ser Leu Leu Phe Ile
                285                 290                 295 gct ggt cat gat acc aat ctt gca aat ctc agt ggg gta ttt gat ctt     1008
Ala Gly His Asp Thr Asn Leu Ala Asn Leu Ser Gly Val Phe Asp Leu
                300                 305                 310 aac tgg tct cta cct ggg cag cca gat aat aca cct cct ggc ggg gag     1056
Asn Trp Ser Leu Pro Gly Gln Pro Asp Asn Thr Pro Pro Gly Gly Glu
315                 320                 325                 330 ctg gtt ttc gaa aga tgg acg cga gtg agt gat aac act gac tgg att     1104
Leu Val Phe Glu Arg Trp Thr Arg Val Ser Asp Asn Thr Asp Trp Ile
                335                 340                 345 caa att tcg ttt gtt tat cag act ctt caa caa atg cgt aag ttt aaa     1152
Gln Ile Ser Phe Val Tyr Gln Thr Leu Gln Gln Met Arg Lys Phe Lys
                350                 355                 360 cct ttt tca tct tcg ctc cca aac aag att gtg ctt acg ttg ccc         1200
Pro Phe Ser Ser Ser Leu Pro Asn Lys Ile Val Leu Thr Leu Pro
                365                 370                 375 tct tgc cag gat aaa aat cct gag ggt atg tgt cca tta aag cat ttt     1248
Ser Cys Gln Asp Lys Asn Pro Glu Gly Met Cys Pro Leu Lys His Phe
                380                 385                 390 att gac att gtg cag aca gca cgt att cca caa tgt gca gtg atg gct     1296
Ile Asp Ile Val Gln Thr Ala Arg Ile Pro Gln Cys Ala Val Met Ala
395                 400                 405                 410 gat gta aac cgt taa                                                  1311
Asp Val Asn Arg <210> SEQ ID NO 6
<211> LENGTH: 436
<212> TYPE: PRT
<213> ORGANISM: Citrobacter amalonaticus ATCC 25407

<400> SEQUENCE: 6

Met Asn Thr Leu Leu Phe Arg Leu Ile Met Phe Ile Phe Met Phe Gly
            -20                 -15                 -10

Ser Phe Pro Leu Gln Ala Glu Val Pro Asp Asp Met Lys Leu Glu Arg
        -5                  -1  1               5                  10

Val Val Ile Val Ser Arg His Gly Val Arg Ala Pro Thr Lys Phe Thr
```

```
                   15                  20                  25
Pro Leu Met Gln Glu Ile Thr Pro Tyr His Trp Pro Gln Trp Asp Val
                30                  35                  40

Pro Leu Gly Trp Leu Thr Ala Arg Gly Gly Glu Leu Val Thr Glu Met
            45                  50                  55

Gly Arg Tyr Gln Gln Lys Val Leu Ile Asp Asn Gly Val Leu Glu Ser
        60                  65                  70

Asn Val Cys Pro Ser Pro Glu Gln Val Ala Val Ile Ala Asp Thr Asp
 75                  80                  85                  90

Gln Arg Thr Arg Lys Thr Gly Glu Ala Phe Leu Ala Gly Phe Ala Pro
                95                 100                 105

Gly Cys Lys Asn Lys Val His Tyr Gln Lys Asp His Asp Lys Lys Asp
            110                 115                 120

Pro Leu Phe Asn Pro Val Lys Met Gly Val Cys Ala Phe Asn Val Gln
        125                 130                 135

Lys Thr Gln Glu Ala Ile Leu Thr Arg Ala Glu Gly Asn Ile Glu Arg
    140                 145                 150

Tyr Thr Gln Arg Tyr Asp Ser Ala Phe Arg Thr Leu Glu Gln Val Leu
155                 160                 165                 170

Asn Phe Ser Arg Ser Ala Ala Cys Arg Ser Ala Ser Gln Ser Gly Cys
                175                 180                 185

Thr Leu Pro Gly Thr Leu Pro Ser Glu Leu Arg Val Ser Ala Asp Thr
            190                 195                 200

Val Ser Leu Ser Gly Ala Trp Ser Leu Ser Ser Met Leu Thr Glu Ile
        205                 210                 215

Phe Leu Leu Gln Glu Ala Gln Gly Met Pro Glu Val Ala Trp Gly Arg
    220                 225                 230

Ile His Gly Glu Lys Glu Trp Thr Ala Leu Leu Ser Leu His Asn Ala
235                 240                 245                 250

Gln Phe Asp Leu Leu Gln Arg Thr Pro Glu Val Ala Arg Ser Arg Ala
                255                 260                 265

Thr Pro Leu Leu Asp Leu Ile Ser Glu Ala Leu Val Ser Asn Gly Ser
            270                 275                 280

Thr Glu Asn His Tyr Gly Ile Lys Leu Pro Val Ser Leu Leu Phe Ile
        285                 290                 295

Ala Gly His Asp Thr Asn Leu Ala Asn Leu Ser Gly Val Phe Asp Leu
    300                 305                 310

Asn Trp Ser Leu Pro Gly Gln Pro Asp Asn Thr Pro Pro Gly Gly Glu
315                 320                 325                 330

Leu Val Phe Glu Arg Trp Thr Arg Val Ser Asp Asn Thr Asp Trp Ile
                335                 340                 345

Gln Ile Ser Phe Val Tyr Gln Thr Leu Gln Gln Met Arg Lys Phe Lys
            350                 355                 360

Pro Phe Ser Ser Ser Leu Pro Asn Lys Ile Val Leu Thr Leu Pro
        365                 370                 375

Ser Cys Gln Asp Lys Asn Pro Glu Gly Met Cys Pro Leu Lys His Phe
    380                 385                 390

Ile Asp Ile Val Gln Thr Ala Arg Ile Pro Gln Cys Ala Val Met Ala
395                 400                 405                 410

Asp Val Asn Arg

<210> SEQ ID NO 7
<211> LENGTH: 29
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: m is A, or C
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: y is C, or T
<220> FEATURE:
<221> NAME/KEY: misc_feature
<222> LOCATION: (27)..(27)
<223> OTHER INFORMATION: n is a, c, g, or t

<400> SEQUENCE: 7
cgcgtggtga ttgtgtccmg ncayggngt                                    29

<210> SEQ ID NO 8
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: d is A, G, or T
<220> FEATURE:
<221> NAME/KEY: misc_feature
<222> LOCATION: (26)..(26)
<223> OTHER INFORMATION: r is A, or G

<400> SEQUENCE: 8
ccaggttggt atcatggccn gcdatraa                                     28

<210> SEQ ID NO 9
<211> LENGTH: 17
<212> TYPE: DNA
<213> ORGANISM: Artificial sequence
<220> FEATURE:
<223> OTHER INFORMATION: Primer

<400> SEQUENCE: 9
agacttccgc cagcccg                                                 17

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10
aagcagctgg gcagtctgc                                               19

<210> SEQ ID NO 11
<211> LENGTH: 21
<212> TYPE: DNA
<213> ORGANISM: Artificial sequence
<220> FEATURE:
<223> OTHER INFORMATION: Primer
```

```
<400> SEQUENCE: 11
aagcggcgtg aactttgtcg g                                              21

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12
atggggactg gcttcaaccc tg                                             22

<210> SEQ ID NO 13
<211> LENGTH: 29
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (19)..(19)
<223> OTHER INFORMATION: m is A, or C
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: y is C, or T
<220> FEATURE:
<221> NAME/KEY: misc_feature
<222> LOCATION: (27)..(27)
<223> OTHER INFORMATION: n is a, c, g, or t

<400> SEQUENCE: 13
cgcgtggtga ttgtgtccmg ncayggngt                                      29

<210> SEQ ID NO 14
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: d is A, G, or T
<220> FEATURE:
<221> NAME/KEY: misc_feature
<222> LOCATION: (26)..(26)
<223> OTHER INFORMATION: r is A, or G

<400> SEQUENCE: 14
ccaggttggt atcatggccn gcdatraa                                       28

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
tttacgagtg cgctgatcgg                                                20
```

```
<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
ataactgcca cctgttctgg tgacg                                             25

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
actcagggtt tctgcggata cc                                                22

<210> SEQ ID NO 18
<211> LENGTH: 21
<212> TYPE: DNA
<213> ORGANISM: Artificial sequence
<220> FEATURE:
<223> OTHER INFORMATION: Primer

<400> SEQUENCE: 18
aatgccagag gttgcgtggg g                                                 21

<210> SEQ ID NO 19
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 19

Arg His Gly Xaa Arg Xaa Pro
1               5
```